(12) United States Patent
Skinhøj et al.

(10) Patent No.: US 7,070,803 B2
(45) Date of Patent: Jul. 4, 2006

(54) CONTROLLED RELEASE PHARMACEUTICAL COMPOSITION FOR ORAL USE CONTAINING MIDODRINE AND/OR ACTIVE METABOLITE, DESGLYMIDODRINE

(75) Inventors: Annette Skinhøj, Rødovre (DK); Peder Mohr Olsen, Kirke Hyllinge (DK); Poul Bertelsen, Vanløse (DK)

(73) Assignee: Nycomed Austria GmbH, Linz (AT)

( * ) Notice: Subject to any disclaimer, the term of this patent is extended or adjusted under 35 U.S.C. 154(b) by 681 days.

(21) Appl. No.: 09/823,202

(22) Filed: Mar. 29, 2001

(65) Prior Publication Data

US 2002/0034544 A1 Mar. 21, 2002

Related U.S. Application Data

(60) Provisional application No. 60/203,783, filed on May 12, 2000.

(30) Foreign Application Priority Data

Mar. 31, 2000 (DK) ........................ 2000 00549

(51) Int. Cl.
- A61K 9/16 (2006.01)
- A61K 9/22 (2006.01)
- A61K 9/52 (2006.01)

(52) U.S. Cl. ...................... 424/457; 424/458; 424/468; 424/469; 424/490

(58) Field of Classification Search .............. 424/468, 424/469, 457, 489, 490, 484, 451, 458, 459, 424/470, 472, 488, 464
See application file for complete search history.

(56) References Cited

U.S. PATENT DOCUMENTS

| 5,128,144 A | 7/1992 | Korsatko-Wabnegg et al. ........................ 424/464 |
| 5,360,822 A | * 11/1994 | Morino et al. .............. 514/605 |

FOREIGN PATENT DOCUMENTS

| DE | 3935736 | 5/1991 |
| EP | 0164571 A2 | 12/1985 |
| JP | 408048639 A | * 2/1996 |

OTHER PUBLICATIONS

B. Korsatko–Wabnegg et al., Einsatz von Poly–D–(–)–3–hydroxybuttersaure zur Formulierung von Manteltabletten mit "Delayed–release"–Effekt, Pharmazie, vol. 46, pp. 204–206 (1991)l.

B. Korsatko–Wabnegg, "Entwicklung von Manteltabletten mit "controlled–release" Effekt auf der Basis von Poly–D–(–)–3–hydroxybuttersaure", Pharmazie, vol. 45, pp. 842–844 (1990).

* cited by examiner

Primary Examiner—James M. Spear
(74) Attorney, Agent, or Firm—Edwards & Angell, LLP; Peter F. Corless; Dianne M. Rees

(57) ABSTRACT

Novel controlled release pharmaceutical compositions for oral use containing midodrine and/or its active metabolite desglymidodrine. The novel compositions are designed to release midodrine and/or desglymidodrine after oral intake in a manner which enables absorption to take place in the gastrointestinal tract so that a relatively fast peak plasma concentration of the active metabolite desglymidodrine is obtained followed by a prolonged and relatively constant plasma concentration of desglymidodrine.

The novel compositions may be designed for administration once or twice daily, i.e. a therapeutically effective concentration of desglymidodrine is maintained for a period of at least 10–16 hours followed by a wash out period of about 8–12 hours in order to avoid the well-known midodrine related side effect with respect to supine hypertension. The therapeutically effective concentration of desglymidodrine is regarded as a plasma concentration of desglymidodrine of at least about 3 ng/ml. A composition is designed to release midodrine and/or desglymidodrine in at least the following consecutive steps: i) an initial relatively fast release of midodrine and/or desglymidodrine (in order to obtain a relatively fast onset of action), ii) a steady release or a slower release than in step 1 of midodrine and/or desglymidodrine (in order to maintain a plasma concentration of desglymidodrine which is prolonged and relatively constant), iii) a second rise in release of midodrine and/or desglymidodrine (in order to take advantage of absorption from the colon, i.e. such a second rise release is designed to take place when the composition (or the disintegrated parts of the composition) reaches the colon; normally this is regarded to take about 8 hours after oral intake, and iv) a decline in release rate corresponding to that essentially all midodrine and/or desglymidodrine have been released from the composition.

Also disclosed is a method for treating orthostatic hypotension and/or urinary incontinence, the method comprising administration to a patient in need thereof of an effective amount of midodrine and/or desglymidodrine in a composition according to the invention.

27 Claims, 25 Drawing Sheets

CONTROLLED RELEASE PHARMACEUTICAL COMPOSITION FOR ORAL USE CONTAINING MIDODRINE AND/ OR ACTIVE METABOLITE, DESGLYMIDODRINE

This application claims priority to U.S. Provisional Application No. 60/203,783, filed May 12, 2000 and is incorporated herein introduction by reference.

The present invention relates to novel controlled release pharmaceutical compositions for oral use containing midodrine and/or its active metabolite desglymidodrine.

The novel compositions are designed to release midodrine and/or desglymidodrine after oral intake in a manner which enables absorption to take place in the gastrointestinal tract so that a relatively fast peak plasma concentration of the active metabolite desglymidodrine is obtained followed by a prolonged and relatively constant plasma concentration of desglymidodrine.

The novel compositions are also designed for administration once or twice daily, preferably once daily, i.e. a therapeutically effective concentration of desglymidodrine is maintained for a period of at least 10–16 hours followed by a wash out period of about 8–12 hours in order to avoid the well-known midodrine related side effect with respect to supine hypertension. In the present context a therapeutically effective concentration of desglymidodrine is defined as a plasma concentration of desglymidodrine of at least about 3 ng/ml such as, e.g. at least about 3.2 ng/ml, at least about 3.5 ng/ml, at least about 3.7 ng/ml, at least about 4.0 ng/ml, at least about 4.2 ng/ml, at least about 4.5 ng/ml, at least about 4.7 ng/ml or at least about 5 ng/ml.

In another aspect, the invention relates to a method for treating orthostatic hypotension and/or urinary incontinence, the method comprising administration to a patient in need thereof of an effective amount of midodrine and/or desglymidodrine in a composition according to the Invention.

BACKGROUND OF THE INVENTION

Controlled release midodrine compositions are known from the prior art, e.g. U.S. Pat. No. 5,128,144 (Korsatko-Waabnegg et al.). EP-B-0 164 571 (CL Pharma Aktiengesellschaft) and AT-B-383 270 (Chemie Linz Aktiengesellschaft). However, in none of these documents are any compositions intended for less frequent administration such as, e.g. once or twice daily and furthermore, there is no indication of absorption of midodrine (or its active metabolite) from the colon.

DISCLOSURE OF THE INVENTION

Midodrine is a prodrug, which is activated within the human body by an enzymatic hydrolysis to release the therapeutically active metabolite desglymidodrine. Desglymidodrine acts by a stimulation of $\alpha_1$ receptors. Midodrine is used in the treatment of symptomatic orthostatic hypotension. Disorders causing orthostatic hypotension are e.g., Generalized Primary Autonomic Failure
ξ Pure autonomic failure or idiopathic orthostatic hypotension (Bradbury-Eggleston syndrome)
ξ Pure autonomic failure with multiple-system atrophy or Shy-Drager syndrome
ξ Acute pandysautonomia (panautonomic neuropathy)
ξ Familial dysautonomia (Riley-Day syndrome)
Partial Primary Autonomic Failure
ξ Dopamine E-hydroxylase deficiency
ξ Postural orthostatic tachycardia syndrome (length-dependent autonomic neuropathy)
ξ Monoamine oxidase deficiency
ξ Pure vasomotor failure
Disorders of Idiopathic Orthostatic Intolerance
ξ Postural orthostatic tachycardia syndrome
ξ Mitral valve prolapse
ξ Due to prolonged bed rest or space flight
ξ Due to asthenic habitus
Disorders of the Central Nervous System
ξ Tumors (hypothalamic, parasellar, posterior fossa)
ξ Multiple cerebral infarcts
ξ Wernicke's encephalopathy
ξ Tabes dorsalis
ξ Traumatic and inflammatory myelopathies
ξ Parkinson's disease
ξ Hereditary system degenerations
ξ Syringomyelia
ξ Dysautonomia of advanced age
ξ Multiple sclerosis
Systemic Diseases with Autonomic Neuropathy
ξ Botulism
ξ Diabetic neuropathy
ξ Primary systemic amyloidosis
ξ Guillain-Barré syndrome
ξ Porphyria
ξ Lambert-Eaton myasthenic syndrome
ξ Paraneoplastic autonomic neuropathy
ξ Uremic neuropathy
ξ Connective tissue disease
ξ Tangier and Fabry's diseases
ξ Vincristine and heavy metal neuropathies
ξ Leprosy
ξ $B_{12}$ deficiency
ξ Chronic Chagas' disease
ξ Propafenone neuropathy (16)
Endorcine-metabolic Disorders
ξ Primary and secondary adrenocortical insufficiency
ξ Pheochromocytoma
ξ Marked potassium depletion
ξ Severe hypoaldosteronism
Latrogenic Causes
ξ Antihypertensive drugs (Δ-methyldopa, guanethidine, prazosin, E blockers)
ξ Psychotropic drugs (phenothiazines, butyrophenones)
ξ Antiparkinsonian drugs (Sinemet, Parlodel)
ξ Vasodilator drugs (nitrates)
ξ Certain illicit drugs (marijuana)
ξ Thoracolumbar sympathectomy
Disorders with Diminished Cardiac Output
ξ Reduced intravascular volume
ξ Acute and chronic blood loss
ξ Fluid loss due to vomiting, diarrhea, diuretics
ξ Gastrectomy with the dumping syndrome
ξ Salt-losing nephropathy
ξ Altered capillary permeability
ξ Impaired venous return
ξ Severe varicose veins
ξ Venous obstruction (late pregnancy)
ξ Reflex and pharmacologic vasodilatation
ξ Muscle wasting and prolonged recumbency
ξ Intrinsic cardiac disease
ξ Myocardial infarct
ξ Arrhythmias
ξ Restrictive pericardial/myocardial diseases
Miscellaneous Causes
ξ Hyperbradykinnism
ξ Chronic renal hemodialysis
ξ Anorexia nervosa ξ Reduced aortic compliance
ξ Mastocytosis
ξ Baroreflex failure.

Furthermore, midodrine may be used in disorders retrograde ejaculation; disorder of semen ejaculation, or to attenuate symptoms of chronic orthostatic hypotension due to autonomic failure in patients with Bradbury-Eggleston, Shy-Drager syndromes, diabetes mellitus disease and Parkinson's disease.

Midodrine is approved in a variety of European and overseas countries including the U.S.A. mainly for the treatment of symptomatic orthostatic hypotension.

FDA has recommended a dosing of midodrine of up to 10 mg 3 times daily for the treatment of hypotension. According to FDA, the latest dose must not be given later than 6 pm for safety reasons in order to avoid or reduce the risk of supine hypertension. Other countries recommend that the latest dose must not be given later than 4 hours before bedtime.

Midodrine for use in stress urinary incontinence is a very promising use with a tremendous market potential also due to the ageing population. Current conservative therapeutic approaches are α-sympathomimetics, pelvic floor exercises and estrogens, or surgery, which are rather complementary than competitive.

Due to the rather short half-life of the active metabolite of approximately 3 hours midodrine normally must be administered 2–4 times daily. Considering the chronic nature of the diseases in question, which requires a long-term treatment as well as the correlation between plasma levels and the incidence and severity of adverse events, the development of a controlled release form is highly desired.

It has now been found that absorption takes place through the whole gastrointestinal tract. Thus, it has been found that when midodrine reaches to colon (about 8 hours after intake of a single unit capsule containing midodrine) the prodrug midodrine is not measured in plasma at least not at a therapeutic level while the extent of absorption of the active metabolite is identical to that of a solution. In other words, with respect to absorption from the colon it has been found that it is not midodrine, which is measured after oral intake of midodrine but instead it is the active metabolite desglymidodrine itself.

After colon absorption a maximum plasma concentration of desglymidodrine is found to take place at approximately 3 hours after application, i.e. $t_{max}$ corresponds to approx. 3 hours. In contrast thereto, a $t_{max}$ of about 1–2 hour for desglymidodrine is observed after oral intake of midodrine and the corresponding value for midodrine itself is a $t_{max}$ of about 30 min.

The finding that midodrine is converted to the active metabolite before or during absorption from the colon is of importance with respect to the present invention. A further important issue is the fact that FDA has recommended that the latest dose of midodrine is taken not later than 6 pm for safety reasons, thus a wash out period through the night is desirable.

Based on the above findings, the present inventors have developed a controlled release composition for oral use containing midrodrine and/or desglymidodrine and the composition is designed to the release of midodrine and/or desglymidodrine in at least the following consecutive steps:

Step 1 an initial relatively fast release of midodrine and/or desglymidodrine (in order to obtain a relatively fast onset of action),
Step 2 a steady release or a slower release than in step 1 of midodrine and/or desglymidodrine (in order to maintain a plasma concentration of desglymidodrine which is prolonged and relatively constant),
Step 3 a second rise in release of midodrine and/or desglymidodrine (in order to take advantage of absorption from the colon, i.e. such a second rise release is designed to take place when the composition (or the disintegrated parts of the composition) reaches the colon; normally this is regarded to take about 8 hours after oral intake, and
Step 4 a decline in release rate corresponding to that essentially all midodrine and/or desglymidodrine have been released from the composition.

The above release pattern is contemplated in order to obtain the desired plasma concentration of desglymidodrine during day and night after administration orally once daily. Thus, the release pattern above is based on the following requirements with respect to the plasma concentration of desglymidodrine:

1. an initial rise in plasma concentration until a peak concentration is reached (in the present context "a peak concentration" is intended to mean a peak value, a shoulder value or a plateau value in the concentration),
2. a relatively constant plasma concentration of desglymidodrine for approximately about 4.5–14 hours such as, e.g., about 5–14 hours, about 6–14 hours, about 7–14 hours, about 8–13 hours, about 9–13 hours, about 10–14 hours, about 10–13 hours, or such as, e.g. for at least about 4.5 hours, at least about 5 hours, at least about 6 hours, at least about 7 hours, at least about 8 hours, at least about 9 hours, at least about 10 hours, or at least about 11 hours. In some cases, the constant plasma concentration of desglymidodrine may last for at least about 12 hours, at least about 13 hours or at least about 14 hours,
3. a decline in plasma concentration with a half-life of e.g. about 3–4 hours to avoid supine hypertension but other half-lives may also be acceptable e.g. reflecting a continuous release of midodrine and/or desglymidodrine from the composition.

Compositions according to the invention are therefore designed based on the following principle: the term "part" is intended to include a separate part within the composition (the composition may contain pellets of e.g. two different types, or an integrated element of the composition, e.g. a multilayer tablet):

1. The composition contains a part intended for relatively fast release of midodrine and/or desglymidodrine
2. The composition contains a part intended for prolonged release of midodrine and/or desglymidodrine and the prolonged release is intended to last for at least about 7–8 hours.
3. The composition contains a part intended to release midodrine and/or desglymidodrine relatively fast when the composition (or the disintegrated parts of the composition) reaches the colon, i.e. about 6–10 hours such as, e.g., about 8 hours after oral administration.
4. The release of midodrine and/or desglymidodrine from a composition according to the invention is terminated at the most about 12–16 hours after administration in order to obtain a wash out period during night.

In one aspect the invention relates to a controlled release pharmaceutical composition for oral use comprising midodrine or a pharmaceutically acceptable salt thereof and/or its active metabolite desglymidodrine (ST 1059) or a pharmaceutically acceptable salt thereof, the composition being adapted to release midodrine and, when present, desglymidodrine in such a manner that a relatively fast peak (or shoulder or plateau) plasma concentration of desglymidodrine is obtained and that a therapeutically effective plasma concentration of desglymidodrine is maintained for at least about 9 hours such as, e.g. at least about 10 hours, at least about 11 hours., at least about 12 hours, at least about 13 hours, or at least about 14 hours.

More specifically, a relatively fast peak (or shoulder or plateau) plasma concentration of desglymidodrine is obtained about 15 min–6 hours such as, e.g. about 0.5–6 hours, about 1–6 hours, about 2–5.5 hours, or about 2.5–5.2 hours after oral administration of a composition according to the invention.

As mentioned above, it is important to keep the plasma concentration at a relatively constant level and, therefore, the plasma concentration of desglymidodrine after administration of midodrine and/or desglymidodrine is preferably maintained at a therapeutically active level for about 5–16 hours, such as, e.g., about 6–16 hours, about 7–16, about 8–15, about 9–15, about 10–15, about 11–14, about 12–14 or about 13, or for at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours or at least about 16 hours.

In the present context, the term "relatively constant level" means that n is n±60%, such as, e.g., n±50% or n±40% and wherein n is the plasma concentration in ng/ml and monitored in a healthy person. The determination of the "relatively constant level" is performed as described in Example 15 herein.

In principle, relevant active drug substances for use in a composition according to the invention are any drug substance for which a dissolution pattern as described below is of relevance. The most interesting drug substances in this respect and with respect to treatment of orthostatic hypotension and urinary incontinence are the prodrug midodrine and its active metabolite desglymidodrine. In a preferred aspect, a composition according to the invention includes midodrine alone, desglymidodrine alone, or a combination of midodrine and desglymidodrine. Of course such compositions may also contain other active drug substances, if relevant.

Generally, after oral administration of a composition according to the invention containing midodrine, a peak (or shoulder or plateau) plasma concentration of midodrine is obtained 15–90 min after oral administration. Moreover, the plasma concentration of midodrine after oral administration is maintained at a relatively constant level for about 0.7–4 hours such as, e.g. at least about 0.7 hours, at least about 1 hour, at least about 2 hours, at least about 3 hours, or at least about 4 hours.

To this end, the term "relatively constant" is intended to mean m is m±60%, such as, e.g., m±50% or m±40% and wherein m is the plasma concentration in ng/ml and monitored in a healthy person. The determination of the "relatively constant level" is performed as described in Example 15 herein.

In the following further details on a composition according to the invention are given.

Dissolution Requirements

As described in the following, a target plasma profile and release profile can be designed for midodrine and the active metabolite desglymidodrine.

Based on our knowledge of the plasma profile of a midodrine solution and obtained $C_{max}$ values for inactive midodrine and active metabolite desglymidodrine after tablet administration a target in vivo profile has been estimated (FIGS. 1 and 2).

The target profile is based on the findings discussed above and the assumption that it would be preferable to have a fast onset of action and a relatively stable plasma level for 8–11 hours and thereafter to eliminate the drug during the night phase to avoid supine hypertension.

The presumptions made in estimating this target profile were:

i) a fast peak and an effective concentration of the active metabolite for approximately 14 hours are desired from a therapeutic point of view (FDA recommendation: latest dose at 6 pm), ii) the first fraction of the composition should have an absorption rate similar to that of plain tablets, iii) the peak concentration should not be higher than the peak concentration observed after administration of 33% of the total dose in the form of a plain tablet, iv) the plateau level for midodrine should last for approximately 8 hours and for desglymidodrine for approximately 11 hours, v) the drug reaches colon after approximately 8 hours, vi) midodrine is absorbed in the colon with a $t_{max}$ of 3 hours (desglymidodrine) compared to a $t_{max}$ of ½ hour (midodrine) when absorbed in the small intestine, vii) midodrine will not be measured after the colon absorption as midodrine but only as desglymidodrine, viii) $t_{max}$ of desglymidodrine will appear 1 hour after oral administration of midodrine ix) $t_{1/2}$ for midodrine is ½–1 hour and for desglymidodrine 3–4 hours, and x) $C_{max}$ after 7.5 mg midodrine is approximately 11 ng/ml (midodrine) and approximately 3.75 ng/ml (desglymidodrine).

Based on the fact that midodrine plain tablets are dosed from 2.5 mg–10 mg up to 4 times daily and that an individual variation in need for midodrine is known, the level of the target plasma profile may vary a factor 0.1–5. The shape of the profile is more important than the exact level of plasma concentrations.

The estimated target plasma profile has been deconvoluted with plasma concentrations from an oral solution for both midodrine and desglymidodrine to give an estimated in vivo dissolution profile (FIGS. 3 and 4). All data were normalised to a dose of 7.5 mg before deconvolution. In the deconvolution a time interval of 0.5 hours was employed (cf: Langenbucher F., Möller H. Correlation of in vitro drug release with in vivo response kinetics. Part I: mathematical treatment of time functions. Pharm. Ind. 1983; 45:623–8, and Langenbucher F., Möller H. Correlation of in vitro drug release with in vivo response kinetics. Part II: Use of function parameters Pharm. Ind. 1983; 45:629–33).

The presumption in making this deconvolution was that the daily dose of midodrine is the same irrespective of whether the new CR composition or a plain tablet or a solution were administered.

Using this deconvolution, the in vitro dissolution profile for a composition according to the invention is estimated. Presumptions for this estimation are:

i) the in vitro—in vivo correlation will be 1:1 ii) it is possible with the new invention to make a product with essential 100% release after 10–14 hours iii) midodrine is absorbed as such or as the active metabolite through the whole gastrointestinal tract (including colon) in order not to loose any amount of active drug substance ready for absorption into the circulatory system.

Target release in vitro profile estimated as described above:

| Time (hours) | % w/w released midodrine |
|---|---|
| 0.5 | 25 |
| 1 | 35 |
| 2 | 39 |
| 3 | 47 |
| 4 | 53 |
| 5 | 60 |
| 6 | 66 |
| 7 | 73 |
| 8 | 80 |
| 9 | 87 |
| 10 | 93 |
| 12 | 100 |

In order to reflect the second rise in release of midodrine corresponding to the time when the composition reaches the colon, the following target profile is also relevant:

| Time (hours) | % w/w released midodrine |
|---|---|
| 0.5 | 25 |
| 1 | 35 |
| 2 | 39 |
| 3 | 47 |
| 4 | 53 |
| 5 | 60 |
| 6 | 66 |
| 7 | 75 |
| 8 | 90 |
| 9 | 95 |
| 10 | 97 |
| 11 | 99 |
| 12 | 100 |

As apparent from the above, an initial relatively fast release of midodrine is suitable and after about 6–8 hours a second rise in release should be observed. Accordingly, a target release rate profile is as follow (the release rate is given in % dissolved/hour):

about 35%/hour about 30 min after start of the dissolution test,
about 12%/hour about 1 hour after start of the dissolution test,
about 6%/hour about 2 hours after start of the dissolution test,
about 7%/hour about 3 hours after start of the dissolution test,
about 6.5%/hour about 4 hours after start of the dissolution test,
about 6.5%/hour about 5 hours after start of the dissolution test,
about 7.5%/hour about 6 hours after start of the dissolution test,
about 12%/hour about 7 hours after start of the dissolution test,
about 10%/hour about 8 hours after start of the dissolution test,
about 3.5%/hour about 9 hours after start of the dissolution test
about 2%/hour about 10 hours after start of the dissolution test,
about 1%/hour about 12 hours after start of the dissolution test.

In FIG. 5 is given a target dissolution profile and a target release rate curve.

As dissolution test any acceptable method may be applied, preferably a method according to USP or Ph.Eur. Throughout the examples 1, 3–10, the following method has been employed: the in vitro dissolution method according to USP and Ph.Eur. employing dissolution apparatus 2 (paddle), 100 rpm, 0.1 N hydrochloric acid as dissolution medium and a temperature of 37° C. It is contemplated that other dissolution media may be suitable as well as another rotation speed.

Reference is given to the claims herein where further details concerning the dissolution patterns and the release rates of a composition according to the invention are given.

Specific embodiments of interest are as follows:

Compositions according the invention, wherein the release pattern of midodrine from the composition—when tested in vitro using Dissolution Method I or II described in the Experimental part herein and employing a basket according to USP and Ph. Eur, 100 rpm, 600 ml 1 N hydrochloric acid as dissolution medium and a temperature of 37° C.—is:

1–15% w/w is released from the composition within the first 30 min after start of the test,
10–35% (25%) w/w is released about 30 min after start of the test,
15–40% (35%) w/w is released about 1 hour after start of the test
20–50% (39%) w/w is released about 2 hours after start of the test,
20–55% (47%) w/w is released about 3 hours after start of the test,
25–75% such as, e.g., 25–65% (53%) w/w is released about 4 hours after start of the test,
30–74% (66%) w/w is released about 6 hours after start of the test,
40–85% (80%) w/w is released about 8 hours after start of the test,
65–100% (93%) w/w is released about 10 hours after start of the test,
90–110% (100%) w/w is released about 12 hours after start of the test.

A release pattern of midodrine from a composition according to the invention—when tested in vitro using Dissolution Method III or IV described herein and employing a basket according to USP and Ph. Eur, 100 rpm, a first dissolution medium with a pH of about 1.0 for the first 2 hours of the testing followed by a second dissolution medium with a pH of about 6.0 for the next 5.5 hours and finally a third dissolution medium with a pH of about 7.5 until the end of the testing, and a temperature of 37° C.—may also be:

1–15% w/w is released from the composition within the first 30 min after start of the test,
10–35% (25%) w/w is released about 30 min after start of the test,
15–40% (35%) w/w is released about 1 hour after start of the test
20–50% (39%) w/w is released about 2 hours after start of the test,
20–55% (47%) w/w is released about 3 hours after start of the test,
26–75% such as, e.g., 25–65% (53%) w/w is released about 4 hours after start of the test,
30–74% (66%) w/w is released about 6 hours after start of the test, 40–95% such as, e.g., 45–85% (80%) w/w is released about 8 hours after start of the test, 65–100% (93%) w/w is released about 10 hours after start of the test, 75–110% (100%) w/w is released about 12 hours after start of the test.

Another release pattern of midodrine from a composition according to the present invention—when tested in vitro employing any of Dissolution Method I, II, III or IV as described herein,—is as follows (±30% w/w such as, e.g., ±25%, ±20%, ±15% or ±10% of the values stated below):

about 25% w/w is released about 30 min after start of the test, about 35% w/w is released about 1 hour after start of the test, about 39% w/w is released about 2 hours after start of the test, about 47% w/w is released about 3 hours after start of the test, about 53–56% such as, e.g., about 53% w/w is released about 4 hours after start of the test, about 66–72% such as, e.g., about 66% w/w is released about 6 hours after start of the test, about 80–85% w/w is released about 8 hours after start of the test, about 93% w/w is released about 10 hours after start of the test, about 100% w/w is released about 12 hours after start of the test.

A still further release pattern of midodrine from a composition according to the invention—when tested in vitro employing any of Dissolution Method I, II, III or IV as described herein—is:

1–15% w/w is released from the composition within the first 30 min after start of the test, 10–35% (25%) w/w is released about 30 min after start of the test, 15–40% (35%) w/w is released about 1 hour after start of the test, 20–50% (39%) w/w is released about 2 hours after start of the test, 20–55% (47%) w/w is released about 3 hours after start of the test, 25–75% such as 25–65% (53%) w/w is released about 4 hours after start of the test, 30–74% (66%) w/w is released about 6 hours after start of the test, 35–65% (75%) w/w is released about 7 hours after start of the test, 45–95% (90%) w/w is released about 8 hours after start of the test, 65–100% (97%) w/w is released about 10 hours after start of the test, 90–110% (100%) wow is released about 12 hours after start of the test.

Another suitable release pattern of midodrine from a composition according to the invention—when tested in vitro employing any of Dissolution Method I, II, III or IV as described herein—is:

1–15% w/w is released from the composition within the first 30 min after start of the test, 15–35% (25%) w/w is released about 30 min after start of the test, 20–40% (35%) w/w is released about 1 hour after start of the test, 25–50% (39%) w/w is released about 2 hours after start of the test, 30–55% (47%) w/w is released about 3 hours after start of the test, 40–75% such as, e.g., 40–65% (53%) w/w is released about 4 hours after start of the test, 50–74% (66%) w/w is released about 6 hours after start of the test, 60–85% (75%) w/w is released about 7 hours after start of the test, 70–95% (90%) w/w is released about 8 hours after start of the test, 80–100% (97%) w/w is released about 10 hours after start of the test, 90–110% (100%) w/w is released about 12 hours after start of the test.

In other aspects, the release pattern of midodrine from a composition according to the invention—when tested in vitro employing any of Dissolution Method I, II, III or IV as described herein—is as follows (±30% w/w, ±20% w/w, ±10% w/w, ±7.5% w/w or ±5% w/w of the values stated below);

about 25% w/w is released about 30 min after start of the test, about 35% w/w is released about 1 hour after start of the test, about 39% w/w is released about 2 hours after start of the test, about 47% w/w is released about 3 hours after start of the test, about 53% w/w is released about 4 hours after start of the test, about 66 w/w is released about 6 hours after start of the test, about 75% w/w is released about 7 hours after start of the test, about 80% w/w is released about 8 hours after start of the test, about 90% w/w is released about 10 hours after start of the test, about 100% w/w is released about 12 hours after start of the test, or about 28% w/w is released about 30 min after start of the test, about 35% w/w is released about 1 hour after start of the test, about 41% w/w is released about 2 hours after start of the test, about 45% w/w is released about 3 hours after start of the test, about 55% w/w is released about 4 hours after start of the test, about 70 w/w is released about 6 hours after start of the test, about 78% w/w is released about 7 hours after start of the test, about 90% w/w is released about 8 hours after start of the test, about 95% w/w is released about 10 hours after start of the test, about 100% w/w is released about 12 hours after start of the test.

As seen in the examples herein it is possible to obtain a release pattern, which corresponds to the above-mentioned values ±7.5% or ±5%.

In another aspect, the invention relates to a composition, wherein the release pattern of midodrine from the composition—when tested in vitro employing any of Dissolution Method I, II, III or IV as described herein—is as follows (±30% w/w, ±20% w/w, ±10% w/w, ±7.5% w/w or ±5% w/w of the values stated below):

about 20% w/w is released about 30 min after start of the test, about 20% w/w is released about 1 hour after start of the test, about 20% w/w is released about 2 hours after start of the test, about 20% w/w is released about 3 hours after start of the test, about 25% w/w is released about 4 hours after start of the test, about 45 w/w is released about 6 hours after start of the test, about 75% w/w is released about 7 hours after start of the test, about 90% w/w is released about 8 hours after start of the test, about 95% w/w is released about 10 hours after start of the test, about 100% w/w is released about 12 hours after start of the test.

In those cases where the pharmaceutical composition according to the invention contains desglymidodrine or a pharmaceutically acceptable salt thereof then the release pattern of desglymidodrine generally follows the patterns given above for midodrine.

If the pharmaceutical composition according to the invention contains midodrine or a pharmaceutically acceptable salt thereof and desglymidodrine or a pharmaceutically acceptable salt thereof, then the release pattern of the sum of midodrine and desglymidodrine is calculated on a molar basis follows the patterns given above for midodrine.

As earlier discussed the release rate of midodrine (and/or desglymidodrine) is important in order to achieve a suitable release pattern. Thus, a pharmaceutical composition according to the present invention normally has a release rate of midodrine—when tested in vitro employing any of Dissolution Method I, II, III or IV—that corresponds to a curve that has a shape corresponding to i) a relatively fast first initial release followed by ii) a steady release or a slower release than in step i) above, which is followed by iii) a second rise in release rate and, finally, iv) a decline in release rate.

In general, the second rise in release rate takes place 5–10 hours such as, e.g., about 5–9 hours, about 6–8 hours after start of the dissolution test, or 6.5–9 hours after start of the dissolution test simulating the time it takes to reach the colon after oral administration.

With respect to the steady release period, it normally starts about 1–3 hours after the start of the dissolution test, and the steady release is maintained for at least 2 hours such as, e.g. at least 3 hours, at least 4 hours, at least 5 hours, at least 6 hours, at least 7 hours, at least 8 hours such as about 6–8 hours.

More specifically, the release rate of midodrine (or desglymidodrine or the sum of midodrine and desglymidodrine on a molar basis)—when tested in vitro employing dissolution apparatus 2 (paddle) according to USP and Ph. Eur, 100 rpm, 0.1 N hydrochloric acid as dissolution medium or any of Dissolution Method I, II, III or IV as described herein and a temperature of 37° C.—in %/hour is as follows (±10–40% such as, eg. ±10–30% or ±10%, ±15% or ±20% of the values stated below):

about 35%/hour about 30 min after start of the test (range e.g. 15–40%/hour), about 12%/hour about 1 hour after start of the test (range e.g 4–15%/hour), about 6%/hour about 2 hours after start of the test (range e.g. 2–10%/hour), about 7%/hour about 3 hours after start of the test (range e.g. 2–10%/hour), about 6.5%/hour about 4 hours after start of the test (range e.g. 2–15%/hour), about 7.5%/hour about 6 hours after start of the test (range e.g. 2–30% such as, e.g., 2–10%/hour), about 10%/hour about 8 hours after start of the test (range e.g. 2–15%/hour), about 2%/hour about 10 hours after start of the test (range e.g. 0–10%/hour), about 1%/hour about 12 hours after start of the test (range e.g. 0–10%/hour).

A pharmaceutical composition according to the invention is normally suitable for administration once or twice daily, and it differs from a plain tablet composition, e.g. Gutron® tablets, in many ways. In the following is given pharmacokinetic values of importance for achievement of a prolonged therapeutic effect of a composition according to the invention. Further details concerning the definition of the parameters and the method of obtaining relevant values are given in Example 15 herein.

When tested as described in Example 15 herein, $W_{50}$ of midodrine (defined as corresponding to the time the plasma concentration curve is or is above 50% of the $C_{max}$ value) is from about 1 to about 9 hours such as, e.g. from about 1.3 to about 8 hours such as, e.g. at least about 1.4 hours, at least about 1.5 hours, or at least about 1.7 hours.

Compared with a standard midodrine composition, $W_{50}$ is increased with a factor of at least 2 such as, e.g., at least 2.5. A suitable comparison is performed against a plain Gutron® tablet administered in the same dose and $W_{50}$ is determined from a plasma concentration versus time curve. The plasma concentration reflects the sum concentration in nmol/l of midodrine and desglymidodrine.

Analogously, $W_{75}$ (T>75% $C_{max}$) is increased with a factor of at least 2 when compared with a plain Gutron® tablet administered in the same dose. $W_{75}$ (T>75% $C_{max}$) is determined from a plasma concentration versus time curve and the plasma concentration reflects the sum concentration in nmol/l of midodrine and desglymidodrine.

Likewise, $W_{50}$ of desglymidodrine (defined as corresponding to the time the plasma concentration curve is or is above 50% of the $C_{max}$ value) is from about 5 to about 12 hours such as, e.g. from about 6 to about 11 hours such as, e.g. at least about 7 hours.

Furthermore, $T_{max}$ is increased with a factor of at least 2 when compared with a plain Gutron® tablet administered in the same dose. $T_{max}$ is determined from a plasma concentration versus time curve and the plasma concentration reflects the sum concentration in nmol/l of midodrine and desglymidodrine.

MRT (mean residence time) is increased with a factor of at least 1.5 such as, e.g., at least 2, at least 2.5 or at least 3 when compared with a plain Gutron® tablet administered in the same dose. MRT is determined from a plasma concentration versus time curve and the plasma concentration reflects the sum concentration in nmol/l of midodrine and desglymidodrine.

MRT for midodrine is at least about 1.5 hours such as, e.g., at least about 2 hours, at least about 2.5 hours or at least about 3 hours, and/or MRT for desglymidodrine is at least about 6 hours such as, e.g., at least about 7 hours, at least about 7.5 hours, at least about 8 hours, at least about 8.5 hours, at least about 9 hours, or at least about 9.5 hours.

Active Drug Substances

As mentioned above, a composition according to the invention is suitable for use for any active drug substance for which a dissolution pattern as described above is of relevance, and which beneficially can be administered only once or twice daily.

With respect to treatment of orthostatic hypotension and the other conditions mentioned above, midodrine and its active metabolite desglymidodrine are drugs of choice.

Midodrine as well as desglymidodrine exist in racemic form and in the form of the two enantiomeric species.

Midodrine is also known as ST 1085, or 2-amino-N-[2-(2,5-dimethoxyphenyl)-2-hydroxyethyl]-acetamide. It may be in present in racemic form, i.e. as (±)-midodrine, (±)-ST 1085, or (±)-2-amino-N-[2-(2,5-dimethoxyphenyl)-2-hydroxyethyl]-acetamide, (±)-2-amino-N-[2-(2, 5dimethoxyphenyl)-2-hydroxyethyl]-acetamide, or in its enatiomeric form as (−)-midodrine, (R)-midodrine, (−)-ST 1085, (R)-ST 1085, (−)-2-amino-N-[2-(2,5-dimethoxyphenyl)-2-hydroxyethyl]-acetamide or (R)-2-amino-N-[2-(2,5-dimethoxyphenyl)-2-hydroxyethyl]-acetamide, or in its other enantiomeric form (+)-midodrine or (S)-midodrine, (+)-ST 1085, or (S)-ST 1085, (+)-2-amino-N-[2-(2,5-dimethoxyphenyl)-2-hydroxyethyl]-acetamide or (S)-2-amino-N-[2-(2,5-dimethoxyphenyl)-2-hydroxyethyl]-acetamide.

Desglymidodrine is also known as ST 1059, alpha-(aminomethyl)-2,5-dimethoxy-benzenemethanol. It may be present in racemic form, i.e. as (±)-desglymidodrine, (±)-ST1059 or (±)-alpha-(aminomethyl)-2,5-dimethoxy-benzenemethanol, or in its enantiomeric form as (−)-desglymidodrine, (R)-desglymidodrine, (−)-ST1059, (R)-ST1059, (−)-alpha-(aminomethyl)-2,5-methoxy-benzenemethanol or (R)-alpha-(aminomethyl)-2,5-dimethoxy-benzenemethanol, or in its other enatiomeric form (+)-desglymidodrine, (S)-desglymidodrine, (+)-ST1059, (S)-ST1059, (+)-alpha-(aminomethyl)-2,5-dimethoxy-benzenemethanol or (S)-alpha-(aminomethyl)-2, 5-dimethoxy-benzenemethanol.

A composition according to the invention may therefore include midodrine in the racemic form (RS), in the enantiomeric form (R), in the enantiomeric form (S) or in mixtures thereof.

In an embodiment according to the invention a composition includes at least 90% w/w such as, e.g., at least 95% w/w, at least 97% w/w, at least 98% w/w, at least 99% w/w of midodrine in the therapeutically active enantiomeric form; and the therapeutically active enantiomeric form of midodrine is (−)-2-amino-N-(β-hydroxy-2,5-dimethoxyphenethyl)-acetamide or the (R) form of midodrine.

In another embodiment according to the invention, a composition contains the active metabolite desglymidodrine (ST 1059), and desglymidodrine is present in the form of (±)-α-(aminomethyl)-2,5-dimethoxy-benzenemethanol (±ST 1059), (+)-α-(aminomethyl)-2,5-dimethoxy-benzenemethanol (+ST 1059), (−)-α-(aminomethyl)-2,5-dimethoxy-benzenemethanol (−ST 1059) or mixtures thereof.

In a still further embodiment a composition according to the invention contains desglymidodrine in the racemic form (RS), in the enantiomeric form (R), in the enantiomeric form (S) or in mixtures thereof, or it contains at least 90% w/w such as, e.g. at least 95% w/w, at least 97% w/w, at least 98% w/w, at least 99% w/w of desglymidodrine is present in the therapeutically active enantiomeric form. The therapeutically active enantiomeric form of desglymidodrine is contemplated to be (−)-α-(aminomethyl)-2,5-dimethoxy-benzenemethanol (−ST 1059) or the (R) form of desglymidodrine ((R) ST 1059).

In a composition according to the invention midodrine and/or desglymidodrine are present in the form of a pharmaceutically acceptable salt such as a salt formed between midodrine and/or desglymidodrine and an inorganic acid such as e.g., a hydrochloride, a hydrobromide, a hydroiodide, a nitrate, a nitrite, a $H_3PO_3$ salt, a $H_3PO_4$ salt, a $H_2SO_3$ salt, a sulfate, a $H_2SO_5$ salt, or a salt formed between midodrine and/or desglymidodrine and an organic acid such as organic acids like e.g. $H_2CO_3$, acetic acid, $C_2H_5COOH$, $C_5H_7COOH$, $C_4H_9COOH$, $(COOH)_2$, $CH_2(COOH)_2$, $C_2H_5(COOH)_2$, $C_3H_6(COOH)_2$, $(C_4H_8(COOH)_2$, $C_5H_{10}(COOH)_2$, fumaric acid, maleic acid, lactic acid, tartaric acid, citric acid, ascorbic acid, benzoic acid, salicylic acid and phthalic acid.

A composition according to the invention may comprise a further active drug substance, i.e. the composition may be in the form of a so-called combination composition comprising at least two different active drug substances. The further active drug substance may be any active drug substance, which beneficially is used in combination with midodrine and/or desglymidodrine. Interesting examples of further active drug substances are steroids like e.g. hydrocortisone or fludrocortisone or somatostin analogoues like e.g. octreotide.

Dosage

In general, the dosage of the active drug substance present in a composition according to the invention depends inter alia on the specific drug substance, the age and condition of the patient and of the disease to be treated.

A composition according to the present inventions aims at a dosage once or twice daily, preferably once daily. In the present context the term "once dally"/"once-a-day" is intended to mean that it is only necessary to administer the pharmaceutical composition once a day in order to obtain a suitable therapeutic and/or prophylactic response; however, any administration may comprise co-administration of more than one dosage unit, such as, e.g. 2–4 dosage units.

In agreement with the above-mentioned definition of "once daily"/"once-a-day", "twice daily"/"twice-a-day" is supposed to mean that it is only necessary to administer the pharmaceutical composition at the most twice a day in order to obtain a suitable therapeutic and/or prophylactic response in the patient.

Irrespective of the above-mentioned definitions of "once" and "twice" daily, a dosage unit constructed to deliver the active ingredient after only one daily administration is preferred. However, due to individual circumstances some patients may need a new dosage after e.g. 7–18 hours such as, e.g. about 7–8 hours or about 12 or about 18 hours if the patient e.g. has abnormal absorption or bowel transit time. If the individual has a relatively fast bowel transit time, some of the active drug substance may be excreted before the full dosage is released.

With respect to midodrine, the normal daily dose is from 2.5 to 10 mg three or up to four times daily (calculated as midodrine hydrochloride), i.e. a daily dose of from about 7.5 mg to about 40 mg in the treatment of orthostatic hypertension. However, the daily dose in the treatment of urinary incontinence may be different and, accordingly, a composition according to the present invention typically contains from about 25 mg to about 50 mg midodrine such as, e.g. 2.5 mg, 5 mg, 7.5 mg, 10 mg, 12.5 mg, 15 mg, 17.5 mg, 20 mg, 25 mg, 30 mg, 35 mg, 40 mg, 45 mg or 50 mg. In the cases, where midodrine is employed in another form, e.g. in another salt form than midodrine hydrochloride, the above-mentioned dosage ranges are of course to be recalculated so that the same dosage is employed on a molar basis.

As discussed above, midodrine may be present as the racemic form or in one of its enantiomeric forms, preferably the therapeutically active enantiomeric form. In those cases where midodrine is present in its therapeutically active enantiomeric form a reduction in the above-mentioned dosage ranges may be relevant.

With respect to the dosage in those cases where desglymidodrine is employed it is envisaged that the same dosages as mentioned above are relevant.

Formulation Techniques

In principle any relevant controlled formulation technique for preparing an oral controlled release composition may be applied. Thus, the dosage form may be in the form of a liquid having e.g. particles dispersed in a dispersion medium or it may be in the form of a single or a multiple unit dosage form intended for use as such as for dispersing in a dispersion medium before use.

In the following is given a short review on general controlled release formulation techniques with an aim of obtaining the type of dissolution profile described above.

Examples of different controlled release technologies are:
1. Single units
    1.1 Coated matrix
    1.2 Double or triple compression
    1.3 Multilayer coating
2. Multiple units
    2.1 Units having a controlled release coating
    2.2 Units having a controlled release matrix
    2.3 Units having a controlled release compression coating
    2.4 Units with a multilayer coating.

Coated Matrix

The idea behind the use of this technology is to coat a sparingly soluble and/or swellable polymer, in which midodrine (and/or any relevant substance such as, e.g. desglymidodrine) is embedded, with an insoluble diffusion barrier. The diffusion of midodrine is controlled by the matrix and the coat. This technique will cover the type of dissolution profile described in step 2 above.

If a soluble outer film layer containing midodrine is applied on the coated matrix, step 1 is achievable too.

Step 3 can be covered by including enteric coated units embedded in the matrix.

Double or Triple Compression

The basic idea for such a formulation is a core of a polymer having midodrine and/or desglymidodrine incorporated. This core is compression coated with a polymer with midodrine incorporated in the same or another concentration than in the core. When triple compression is employed, the coated core is compression coated once more with a polymer with midodrine in the same or another concentration as in the first coat. Finally, the doble or triple compression unit is spray coated and midodrine is incorporated in the coat. However, the concentrations of midodrine in the different coats may vary markedly.

The idea behind the multiple layers is that when the midodrine of the first layer has been almost depleted, the next layer takes over and levels out or changes the release profile. The spray coating with midodrine and/or desglymidodrine gives an immediate burst of the active compound.

Steps 1, 2 and 3 can be covered by use of this technique.

Multilayer Coating

The idea with this type of formulation is to coat an inert core with several layers of diffusion barriers, each barrier containing different concentrations of midodrine. The concentration should be highest in the inner coat and lowest in the outer coat. The purpose of the concentration gradient is to compensate for the increasing diffusion distance closer to the core. If the thickness of the diffusion barriers and the concentration gradients are correctly adjusted, steps 1, 2 and 3 will be obtainable.

Use of Enteric Coating

The correct start of step 3 in the triple compression and multilayer technologies might be optimized by the use of an enteric polymer.

Use of Amylose as Colon Degradable Excipient

The correct start of step 3 in the triple compression and multilayer technologies might also be optimized by the use of an amylose containing film coating such as a coating containing ethylcellulose and amylose or Eudragit RS and amylose.

Multiple Unit Systems

The units comprise pellets, granules, crystals, mini tablets or mixtures thereof.

Step 1 can be covered by an uncoated unit.

Step 2 can be covered by the application of a controlled release coating or by formulating the unit as a matrix or a coated matrix.

Step 3 can be covered by the use of an enteric polymer or amylose, or by having units compressed as described in the triple compression technology.

In specific embodiments, a composition according to the invention is in the form of a solid dosage form such as, e.g., tablets, capsules, sachets, solid dispersion, crystals, granules and the like.

A composition according to the invention can also comprise at least two parts such as at least a first and a second part, each part contains midodrine and/or, if present, desglymidodrine and the first part being adapted to release midodrine and/or, if present, desglymidodrine, in a controlled manner during the first 0–14 such as, e.g. 0–11 hours after oral intake and the second part being adapted to release midodrine and/or, if present, desglymidodrine, starting at least 6 hours after oral intake.

In such a composition at least one of the at least two parts is present in the composition in the form of a multiplicity of individual units such as, e.g. pellets or minitablets.

The two parts of the at least two parts may also be present in the composition in the form of a multiplicity of individual units such as, e.g. pellets or minitablets, and the two parts may be in admixture.

A composition according to the invention may also be in multiple unit dosage form such as, e.g., wherein at least one of the at least two parts comprises at least two different types of pellets, the first type of pellets corresponding to a first fraction and the second type of pellets corresponding to a second fraction.

Moreover, the at least two parts of the composition may comprise at least two different types of pellets, the first type of pellets corresponding to the first part and the second type of pellets corresponding to the second part.

A composition according to the invention may also as individual units contain minitablets, i.e. be in the form of a multiple unit dosage form comprising at least two different types of minitablets, the first type of minitablets corresponding to the first part and the second type of minitablets corresponding to the second part. In the present context a minitablet is a tablet having a size in a range corresponding to from about 0.7 mm to about 7 mm in diameter such as, e.g., in a range corresponding to from about 1 to about 7 mm, from about 1.5 to about 6 mm, from about 2 mm to about 5 mm, from about 2 mm to about 4 mm such as in a range corresponding to from about 2 to about 3 mm in diameter.

A composition according to the invention may also as individual units contain relatively large crystals of the active drug substance. In such cases, the size of the unit is at the most about 1 mm such as, e.g., in a range corresponding to from about 0.1 to about 1 mm, from about 0.2 mm to about 0.8 mm, from about 0.2 mm to about 0.7 mm or from about 0.3 mm to about 0.7 mm.

A composition according to the invention may be in the form of a multiple unit dosage form, wherein the first or the second part is in the form of minitablets, in the form of pellets or in the form of large crystals of the active drug substance.

Moreover, at least two fractions may be present in a tablet such as, e.g. a multilayer tablet and the at least first and the second part are each comprised in a layer in the tablet.

Furthermore, a composition according to the invention may comprise a third part adapted to release midodrine and, if present, desglymidodrine relatively fast from the composition and/or a fourth part adapted to release midodrine and/or desglymidodrine from the composition 6–10 hours after oral intake.

In one embodiment the third and/or, if present, the fourth part comprise pellets or minitablets or are a layer in a tablet.

With respect to release kinetics, a composition according to the invention may have a first part, a second part, a third part and/or a fourth part which have a release kinetic corresponding to a zero or a first order release or a mixture of zero and first order release. Other orders of release may be 1.5, 2, 3 or 4.

Pharmaceutically Acceptable Excipients

Apart from the active drug substance in the composition, a pharmaceutical composition according to the invention may further comprise pharmaceutically acceptable excipients.

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties.

Fillers/diluents/binders may be incorporated such as sucrose, sorbitol, mannitol, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex®10), starches or modified starches (including potato starch, maize starch and rice starch), sodium chloride, sodium phosphate, calcium phosphate (e.g. basic calcium phosphate, calcium hydrogen phosphate), calcium sulfate, calcium carbonate, gelatine, polyvinylpyrrolidone (30, 90, Kollidon VA 64), and sodium carboxymethylcellulose.

Disintegrants may be used such as cellulose derivatives, including microcrystalline cellulose, low-substituted hydroxypropyl cellulose (e.g. LH 11, LH 22, LH 21, LH 20, LH 32, LH 31, LH30); starches, including potato starch; croscarmellose sodium (i.e. cross-linked carboxymethylcellulose sodium salt, e.g. Ac-Di-Sol®); alginic acid or alginates; insoluble polyvinylpyrrolidone (e.g. Polyvidon® CL, Polyvidon® CL-M, Kollidone® CL, Polyplasdone® XL, Polyplasdone® XL-10); sodium carboxymethyl starch (e.g. Primogel® and Explotab®).

Glidants and lubricants may be incorporated such as stearic acid, metallic stearates, talc, waxes and glycerides with high melting temperatures, colloidal silica, sodium stearyl fumarate, polyethylenglycols and alkyl sulphates.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g. docusate sodium and sodium lauryl sulphate) and cationic (e.g., benzalkonium chloride, benzethonium chloride and cetrimide) or mixtures thereof. Examples of amphoteric surfactants are 1,2-diacyl-L-phosphatidylcholine, N-lauryl-N,N-dimethylglycine, alkylaminopropionic acid, alkyliminodipropionic acid, and dimethyl-(3-palmitamidopropyae)-aminoacetate.

Other appropriate pharmaceutically acceptable excipients may include colorants, flavouring agents, pH adjusting agents. sofubilizing agents, wetting agents and buffering agents.

Modified Release Coating

A unit comprised in a composition according to the invention may be coated with a modified release coating.

The modified release coating is a substantially water-insoluble but water-diffusible coating.

The modified release coating may be applied on the multiple units or on the single units from a solution and/or suspension preferably in an aqueous solvent, but an organic coating composition may also be applied. The modified release coating may also be applied as a compression coating comprising a dry mixture of polymer(s) and the e.g. the active drug substance.

Examples of matrix-forming agents are hydroxypropylmethylcellulose such as, e.g., 1828, 2208, 2906 or 2910 according to USP, hydroxypropylcellulose, micronised ethylcellulose, low-substituted hydroxypropylcellulose (LH 20, 21, 31).

Examples of film-forming agents which are suitable for use in accordance with the present invention are agents selected from the group consisting of cellulose derivatives such as, e.g., ethylcellulose, cellulose acetate, cellulose propionate, cellulose butyrate, cellulose valerate, cellulose acetate propionate; acrylic polymers such as, e.g., polymethyl methacrylate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer; silicon polymers such as, e.g., ladder polymer of sesquiphenyl siloxane, and colloidal silica; polycarbonate; polystyrene; polyester; coumarone-indene polymer; polybutadiene; and other high molecular synthetic polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the tradename Eudragit®. In further preferred embodiments, the acrylic coating comprises a mixture of two acrylic resin lacquers commercially available from Rohm Pharma under the tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. Eudragit® RL/RS mixtures are insoluble in water and in digestive fluids. However, coatings formed from the same are swellable and permeable in aqueous solutions and digestive fluids. The Eudragit® RL/RS dispersions may be mixed together in any desired ratio in order to ultimately obtain a modified release formulation having a desirable dissolution profile. The most desirable modified release formulations may be obtained from a retardant coating based on Eudragit® NE 30D, which is a neutral resin having a molecular weight of 800,000.

Examples of enteric polymers are cellulose acetate phthalate, cellulose acetate trimellitate, hydroxy propyl methyl cellulose acetate phthalate, hydroxy propyl methyl cellulose acetate succinate, carboxy methyl ethyl cellulose, polyvinyl acetate phthalate, copolymer of vinyl acetate and crotonic acid and poly(methacrylic acid, ethacrylate), and Eudragit® S 12.5, Eudragit® S 100, Eudragit® FS 30D (all from Röhm), Sureteric® (from Colorcom), Aquateric® (from FMC) or HPMCP (from Shin-Etsu).

The amount of coating applied is adapted so as to obtain a predetermined dissolution characteristic of the composition.

However, the amount of coating applied should also be adapted so that there will be no rupturing problems.

The coating may be admixed with various excipients such as plasticizers, anti-adhesives such as, e.g., colloidal silicium dioxide, inert fillers, lipophilic agents such as, e.g, stearic acid, capric acid or hydrogenated castor oil, colon targeting excipients such as, e.g. amylose, ethylcellulose, Eudragit S 12.5 etc., and pigments in a manner known per se.

Tackiness of the water-dispersible film-forming substances may be overcome by simply incorporating an anti-adhesive in the coating. The anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates. hydrogenated aluminium silicates, hydrous aluminium potassium silicates and talc. The preferred anti-adhesive is talc. The anti-adhesive or mixture of anti-adhesives is preferably incorporated in the coating in an amount of about 0.1–70% by weight, in particular about 1–60% by weight, and preferably about 8–50% by weight of the film layer. By selecting a small particle size of the talc, a larger surface area is obtained; the consequent higher anti-adhesive effect makes it possible to incorporate smaller amounts of specific anti-adhesives.

The units may further comprise an outer film layer.

In one aspect, the outer second layer comprises a water-based film-forming agent which prevents adhesion between the units at elevated temperatures and imparts flowability to the units, the water-based film-forming agent being anti-adhesive at temperatures above about 40° C., especially temperatures above about 50° C., such as a temperature between about 60° C. and about 120° C., and being selected from diffusion coating materials such as ethylcellulose or enteric coating materials such as anionic poly(meth)acrylic acid esters, hydroxypropylmethylcellulosephthalate, celluloseacetatephthalate, polyvinylacetatephthalate, polyvinylacetatephthalatecrotonic acid copolymerisates, or mixtures thereof, or water-soluble coating materials such as water-soluble cellulose derivatives, e.g. hydroxypropylcellulose, carboxymethyleellulose, methyloellulose, propyloellulose, hydroxyethyleellulose, carboxyethylcellulose, carboxymethylhydroxyethylcellulose, hydroxymethylcellulose, carboxymethylethylcellulose, methylhydroxypropylcellulose or hydroxypropylmethylcellulose.

Examples of plasticizers for use in accordance with the present invention include triacetin, acetylated monoglyceride, rape oil, olive oil, sesame oil, acetyl tributyl citrate, acetyl triethyl citrate, glycerin, sorbitol, diethyfoxalate, diethylmalate, diethylmaleate, diethylfumarate, diethylsuccinate, diethylmalonate, dioctylphthalate, dibutylsebacetate, triethylcitrate, tributylcitrate, glyceroltributyrate, polyethyleneglycol, propyleneglycol, 1,2-propyleneglycol, dibutylsebacate, diethylsebacate and mixtures thereof. The plasticizer is normally incorporated in an amount of less than 20% by weight, calculated on the dry matter content of the coating composition.

BRIEF DESCRIPTION OF THE DRAWINGS

The invention is further illustrated in the drawing, wherein

FIGS. 23–24 illustrate the results of Example 15.

Figure 1:
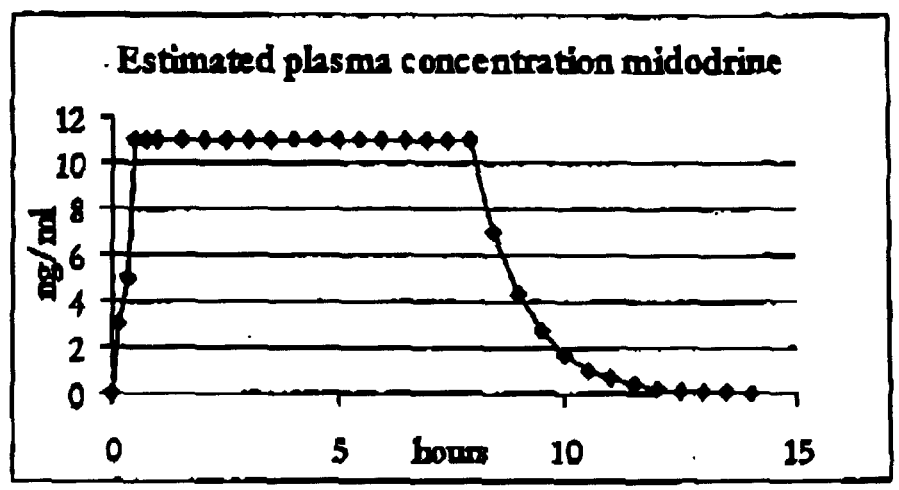
FIG. 1 shows the estimated plasma concentration of midodrine.
Figure 2:
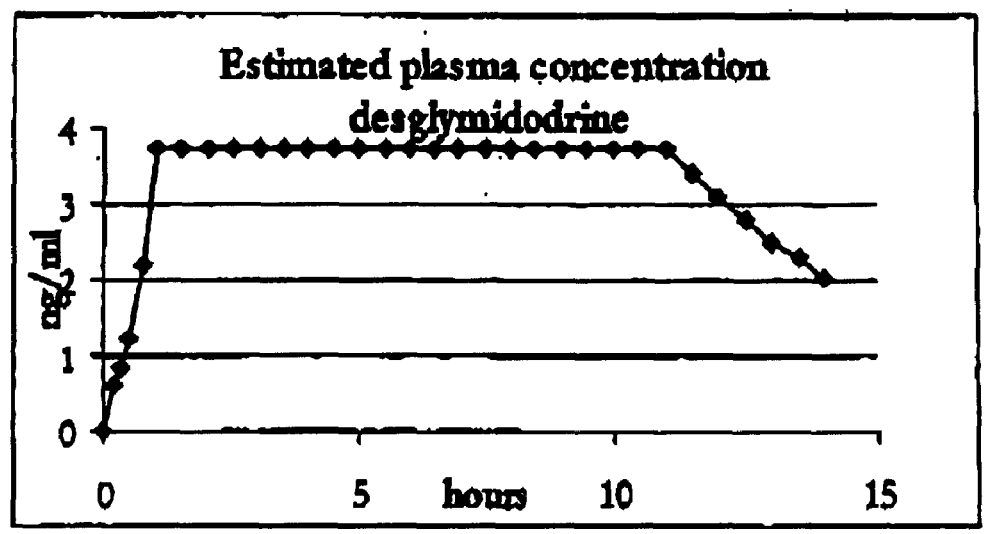
FIG. 2 shows the estimated plasma concentration of desglymidodrine.
Figure 3:
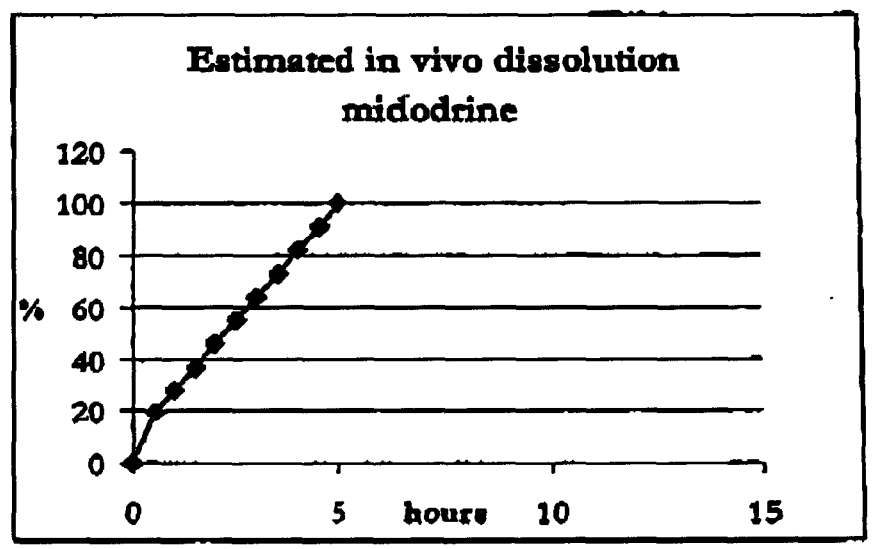
FIG. 3 shows the estimated in vivo dissolution of midodrine.
Figure 4:
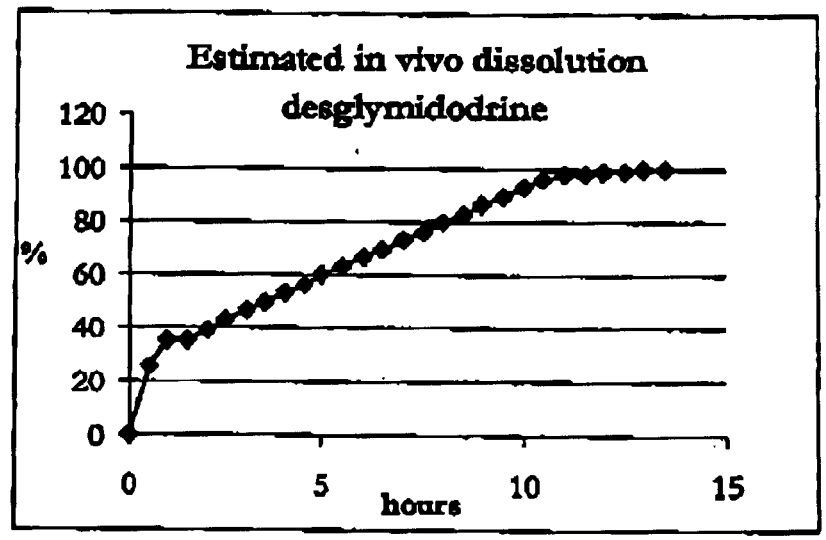
FIG. 4 shows the estimated in vivo dissolution of desglymidodrine.
Figure 5:
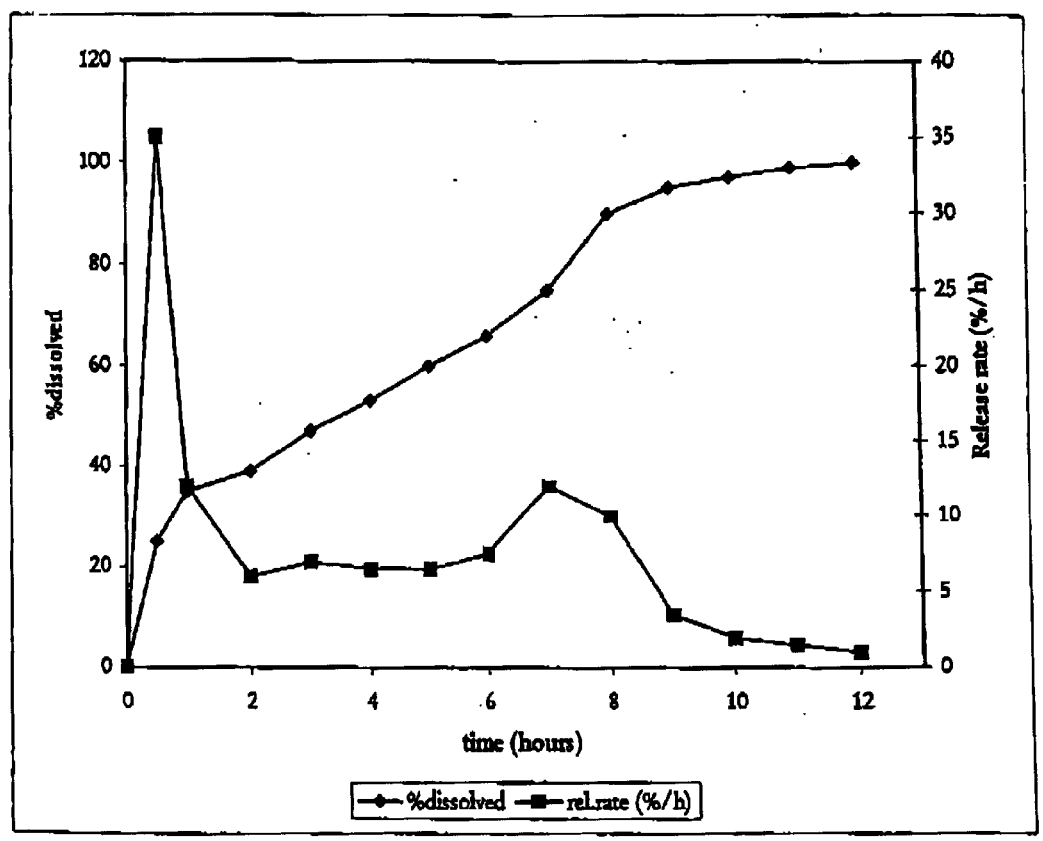
FIG. 5 shows the estimated in vitro target for dissolution of midodrine and the estimated release rate.
Figure 6:
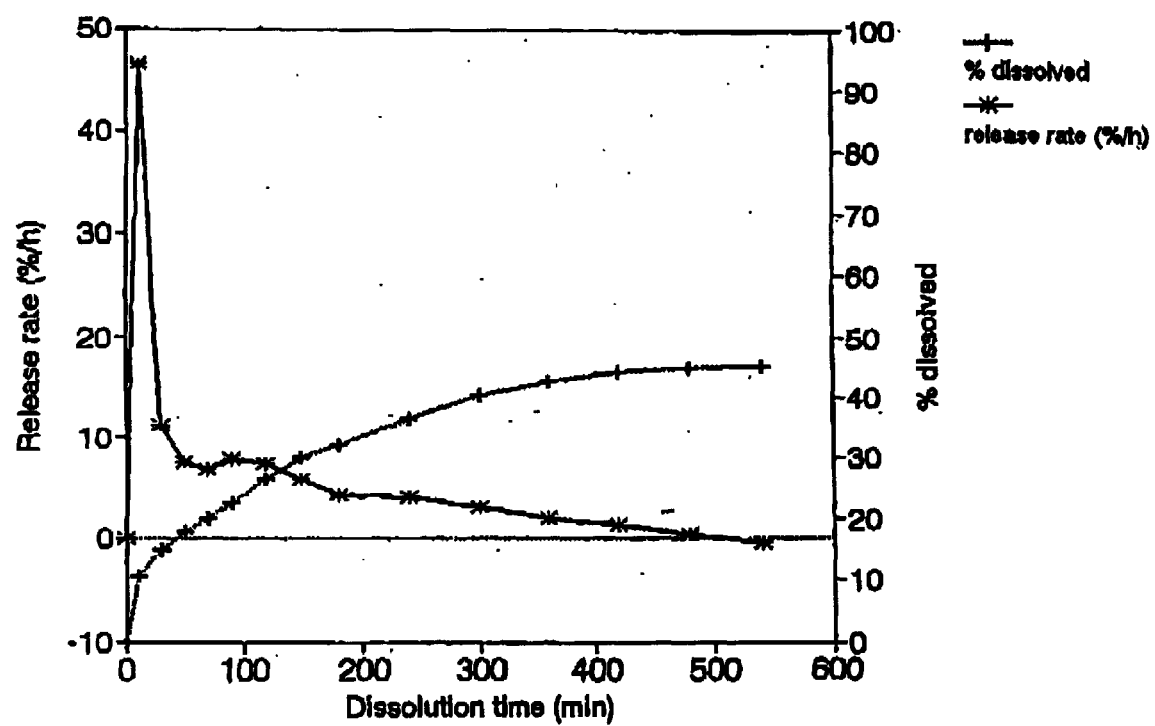
FIGS. 6–9 illustrate the results of Example 1.
Figure 7:
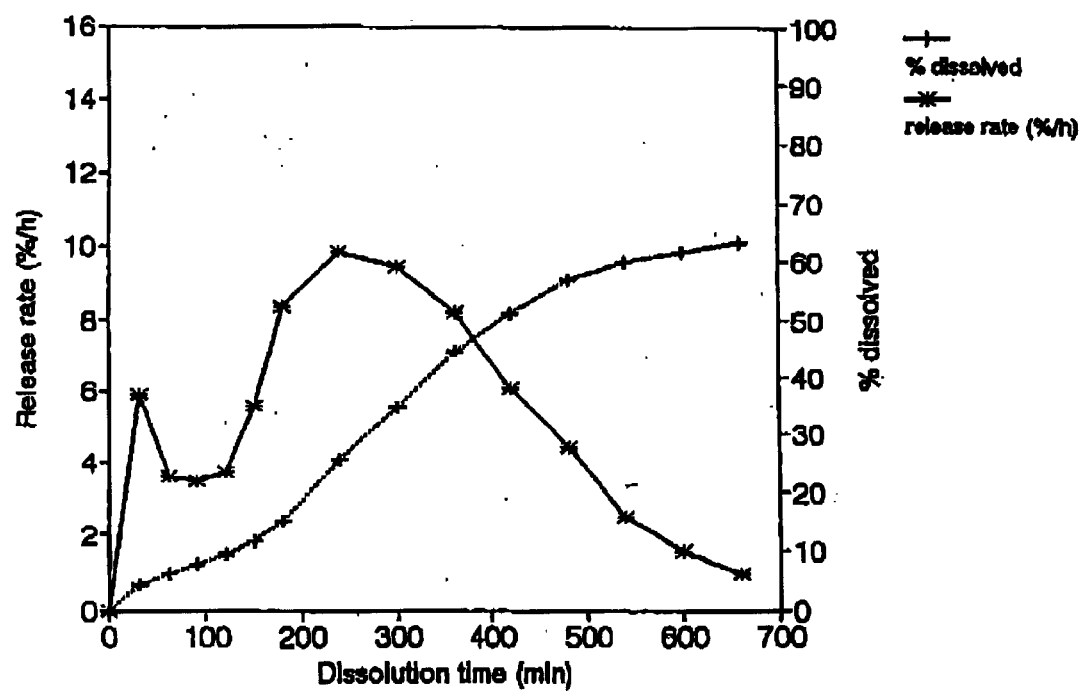
Figure 8:
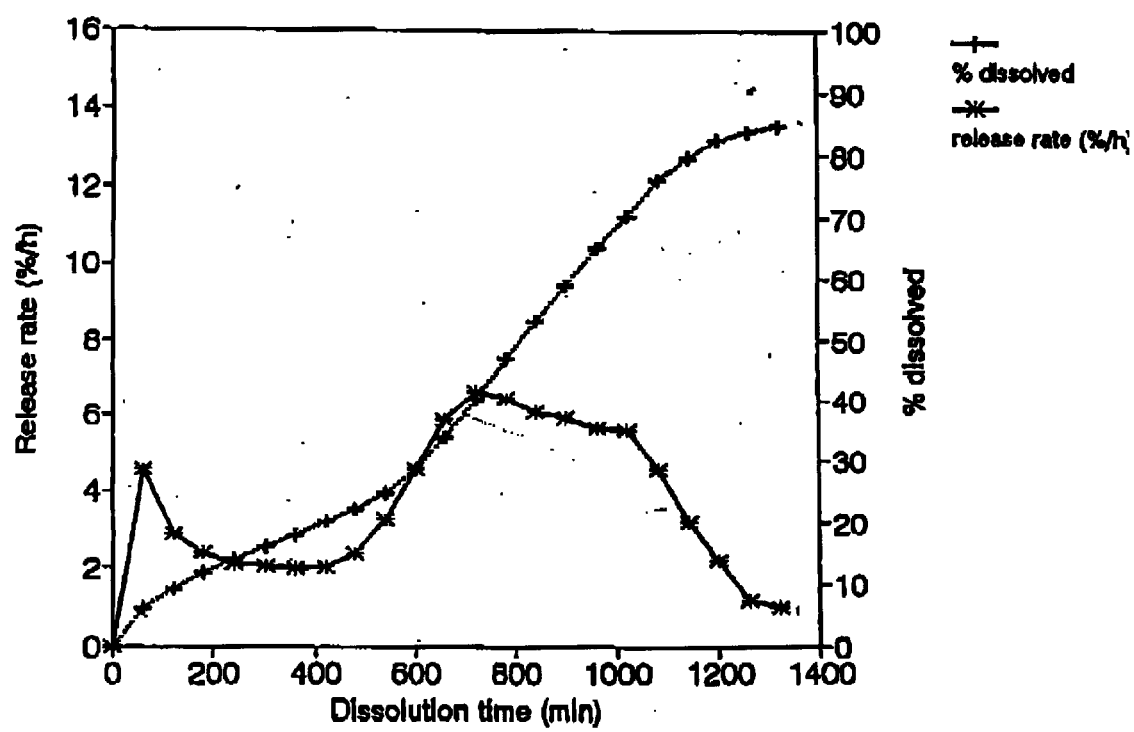
Figure 9:
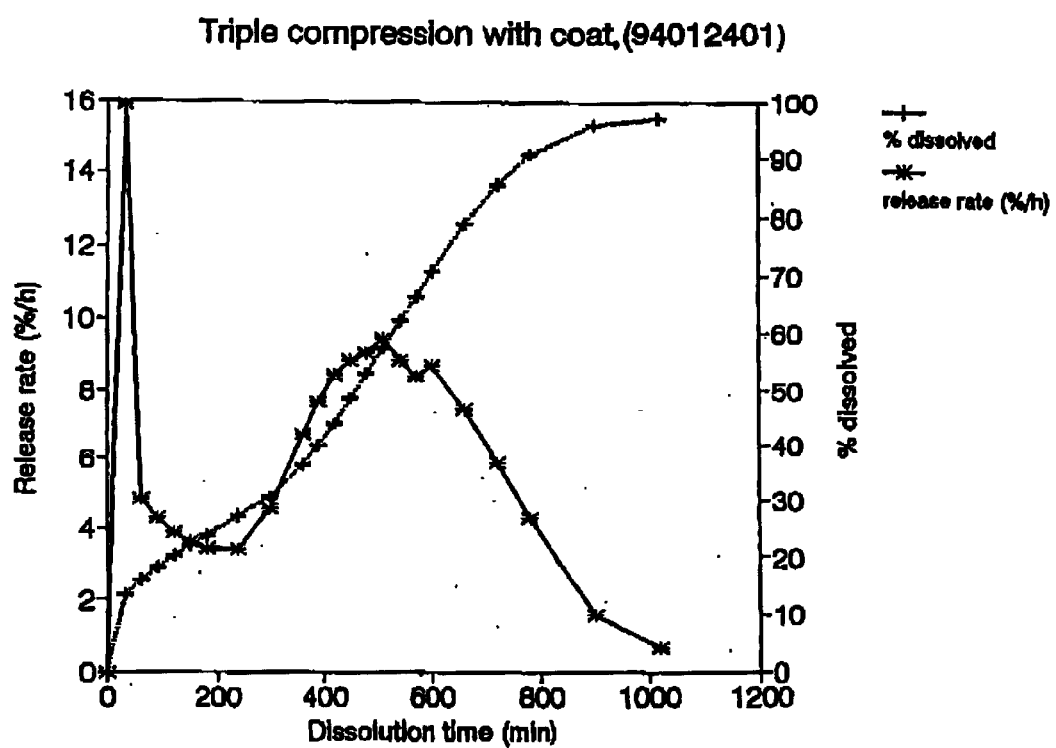
Figure 10:
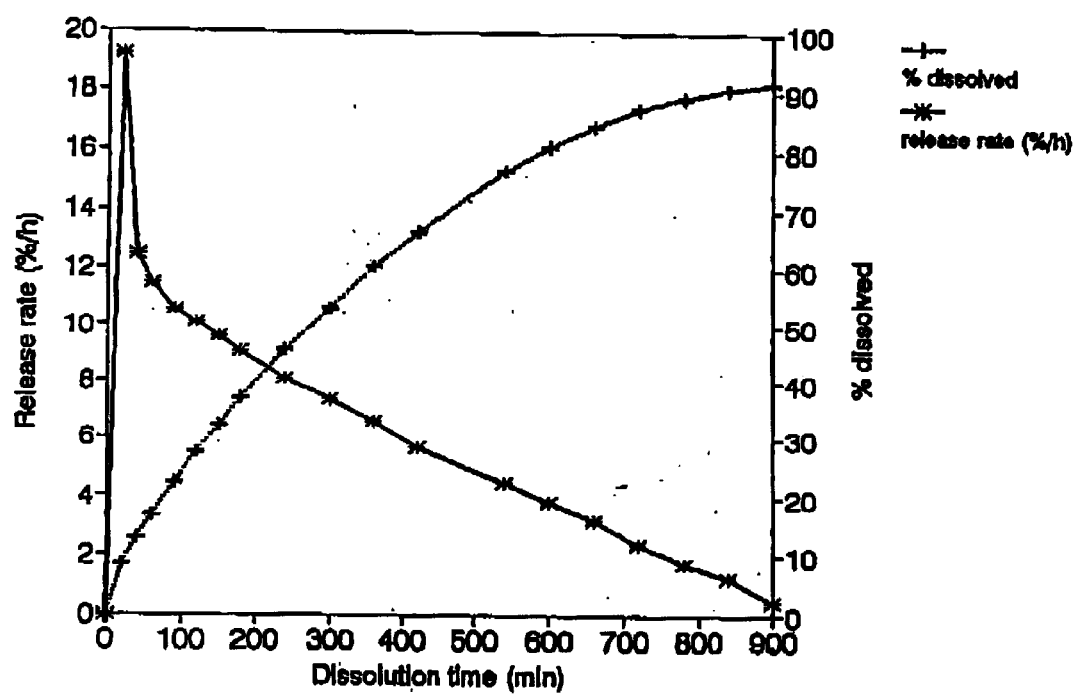
FIGS. 10–13 illustrate the results of Example 3.
Figure 11:
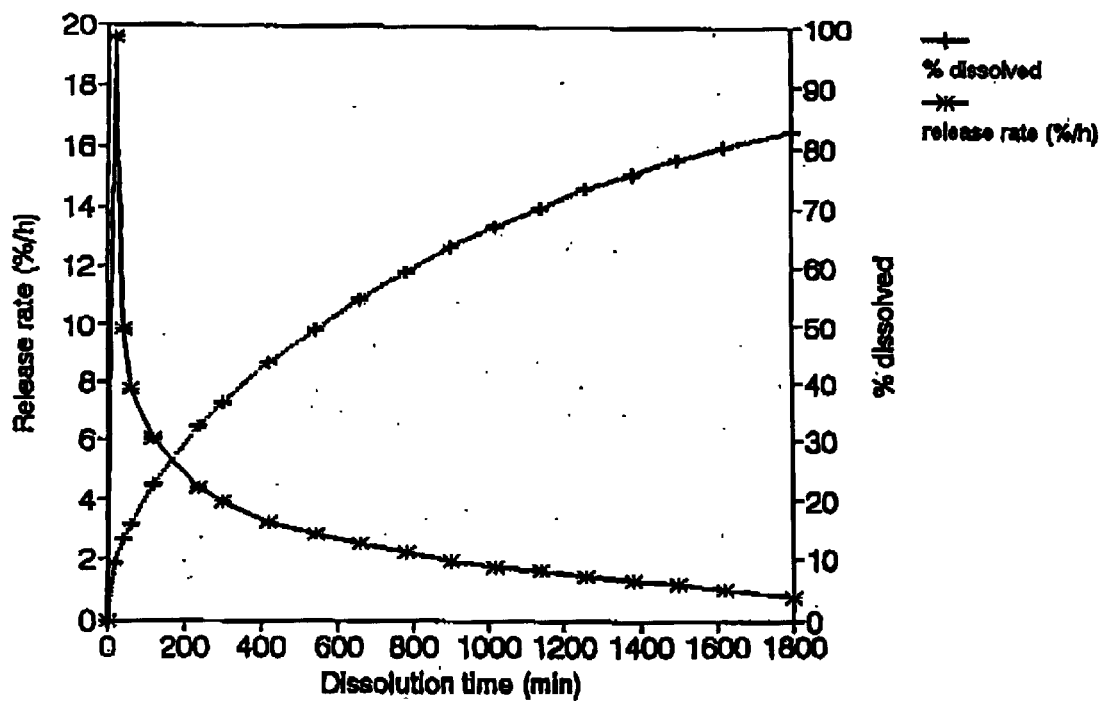
Figure 12:
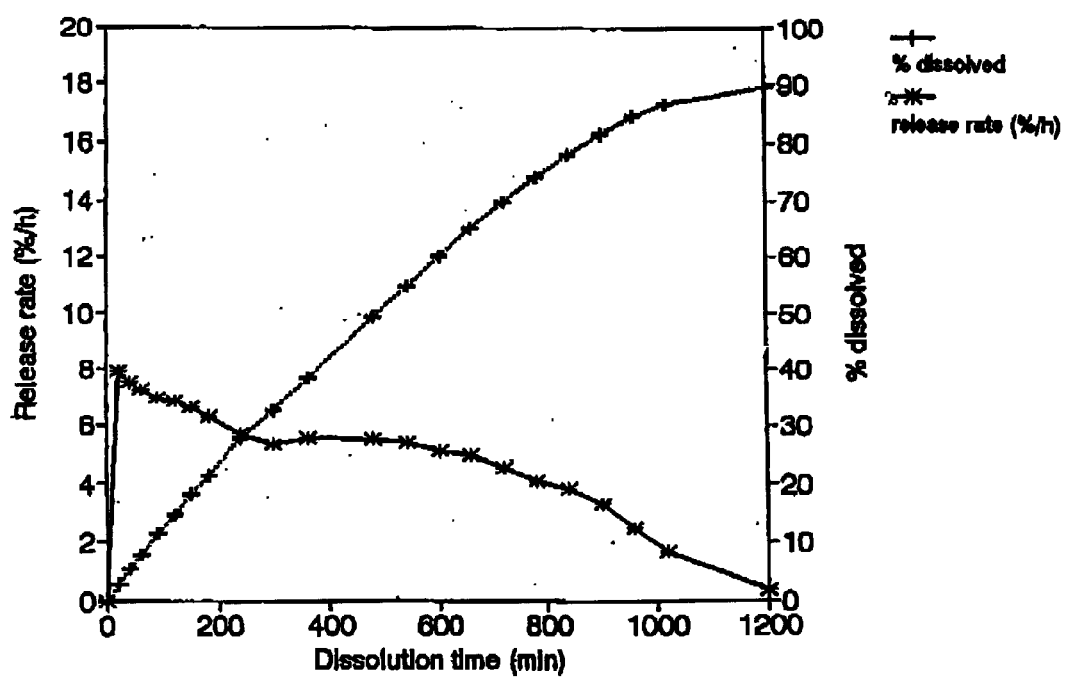
Figure 13:
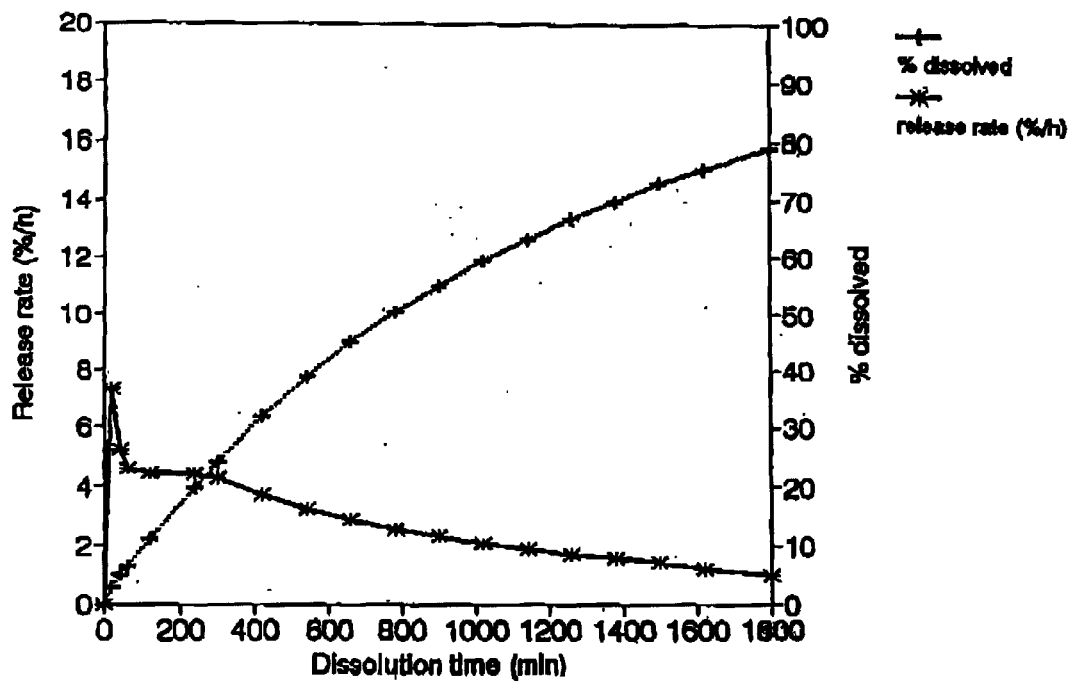

The following examples are intended to illustrate specific embodiments of the present invention but are not intended in any way to limit the invention. Some of the examples are included in order to illustrate that the release rate and dissolution characteristics of a composition can be changed by varying a number of formulation parameters.

Methods

Dissolution Method I for MITAB (Midodrine Hydrochloride Triple Compression Tablets).

| | |
|---|---|
| Apparatus | Ph.Eur/USP dissolution apparatus + Perkin Elmer fully automatic dissolution system + Disslab PC-programme |
| Glass fibre filter | 0.7 µm |
| Dissolution medium | 600 ml 0.1 N HCl |
| Rotation speed | 100 rpm |
| Stirrer | Basket |
| Sampling times | As appear from tables |
| Detection wavelength | 290 nm |
| Measuring equipment | UV-spectrophotometer, 10 mm quartz cuvette |
| Temperature of dissolution medium | 37° C. ± 0.5° C. |

Reagents:

0.1N HCl is prepared by dilution of concentrated HCl (37%) with purified water.

Standards:

Two solutions are prepared with a concentration of 10 µg/ml midodrine hydrochloride in 0.1 N HCl. 0.1 N HCl is used as blind. The absorbances of the solutions are measured on the spectrophotometer.

$E_{1\%/cm}$ is calculated.

$E_{1\%/cm} = A \times 1000$, where 1000 is due to the fact, that the solution is only 0.001%.

The mean value of the to measurements is inserted in the software programme in accordance with the manual for the automated dissolution system.

Performance:

600 ml 0.1N HCl is filled in each of the six vessels in the dissolution equipment. The media is heated to a temperature of 37° C.±0.5° C. One weighed tablet is placed in each of the six baskets. The stirring is started as soon as the baskets are lowered into the vessels. The sample is filtered through a 0.7 µm filter. The absorbances of the filtered samples are measured directly at 290 nm.

Dissolution Method II for MITAB (Midodrine Hydrochloride Triple Compression Tablets). HPLC-detection The dissolution parameters are described in Method I. The measurement is performed by HPLC.

| | |
|---|---|
| Column | Spherisorb ODS-1; 5 µm; 25 cm; ID 4.6 µm |
| Injection volume | 20 µl |
| Flowrate | 1.0 ml/min |
| Mobile phase | Phosphate buffer pH 3: methanol 77:23 (v/v) |
| Detection | 290 nm |
| Runtime | 30 min |

Reagents for dissolution are described in Method I.

Buffer solution pH 3 is prepared by dissolving 23.6 g potassium dihydrogen phosphate in 900 ml purified water. o-Phosphoric acid 85% is used to adjust pH. The flask is filled to 1 l.

Standards:

Two stock solutions with a concentration of midodrine hydrochloride 120 µg/ml in 0.01 N HCl are prepared. The solutions are stored in refrigerator.

Prepare from each stock solution two standard solutions with a concentration of midodrine hydrochloride approximately 1.5 µg/ml and 15 µg/ml respectively, diluted with 0.01N HCl. Desglymidodrine hydrochloride is quantified against the standard curve of midodrine hydrochloride. The relative response factor is 1.25 for Desglymidodrine hydrochloride to midodrine hydrochloride.

Performance:

The dissolution is performed as described in Method I. The sample is withdrawn with a pipette and transferred to a syringe. The sample is filtered through a 0.7 µm filter. The first ml is returned to the vessel in order to reduce deviation from the desired volume. A sample of approximately 1.5–2 ml is transferred to the vial, the rest is returned to the vessel. The absorbances of the filtered samples are measured as described.

Calculations:

A standard curve is calculated by linear regression, using the standard solutions. The peak area of the sample is the sum of the peak area of Midodrine Hydrochloride and the peak area of Desglymidodrine hydrochloride, where the latter is divided by the relative response factor 1.25.

The results are calculated as % released at any time and presented as a mean value of the six samples together with min and max.

$$\% \text{ dissolved} = \frac{A \text{ vol } 100}{b \, x}$$

Where

A sum of peak area of midodrine hydrochloride and Desglymidodrine hydrochloride (corr.)

Vol 600 ml for tablets (MITAB)

100% b slope of the calibration curve (A/mg/ml)

x declared amount (mg)

Dissolution Method III for MICAP (Midodrine Hydrochloride Multiple Unit Capsules).

| | |
|---|---|
| Apparatus | Ph.Eur/USP dissolution apparatus + Perkin Elmer fully automatic dissolution system + Disslab PC-programme |
| Glass fibre filter | 0.7 µm |
| Dissolution medium at the beginning | 600 ml 0.1 N HCl |
| Dissolution media at change to pH 6.0 | Addition of 130 ml 0.23 M $Na_3PO_4$ solution |
| Dissolution media at change to pH 7.5 | Addition of further 70 ml 0.23 M $Na_3PO_4$ solution |
| Time for change to pH 6.0 | 2 hours (120 min) |
| Time for change to pH 7.5 | 7.5 hours (450 min) |

| | |
|---|---|
| Rotation speed | 100 rpm |
| Stirrer | Basket |
| Sampling times | As appear from tables |
| Detection wavelength | 290 nm |
| Measuring equipment | UV-spectrophotometer, 10 mm quartz cuvette |
| Temperature of dissolution medium | 37° C. ± 0.5° C. |
| Reference (vessel no 7) | An empty capsule dissolved in 600 ml 0.1 N HCl |
| Vessel no 7 is added Na$_3$PO$_4$ solution in parallel with the six sample vessels | |

Reagents:

0.1 N HCl is prepared by dilution of concentrated HCl (37%) with purified water. 0.23 M Na$_3$PO$_4$ solution. Dissolve an amount of Na$_3$PO$_4$·12H$_2$O in a bit of 1M HCl-R and add water to a concentration of 0.23 M. (Strong alkaline).

Buffer solution pH 6.0: 600 ml 0.1 N HCl is added 130 ml 0.23 M Na$_3$PO solution.

Buffer solution pH 7.5. Buffer solution pH 6.0 is added further 70 ml 0.23 M Na$_3$PO solution.

Standards:

Two solutions are prepared with a concentration of 10 μg/ml midodrine hydrochloride in 0.1 N HCl. 0.1N HCl is used as blind. The absorbances of the solutions are measured on the spectrophotometer.

$E_{1\%/cm}$ is calculated. It has previously been determined, that the $E_{1\%/cm}$ is the same for the three media, so it is only necessary to perform the test in 0.1N HCl.

$E_{1\%/cm}$=A×1000, where 1000 is due to the fact, that the solution is only 0.001%

The mean value of the to measurements is inserted in the software programme in accordance with the manual for the automated dissolution system.

Performance:

600 ml 0.1N HCl is filled in each of the seven vessels in the dissolution equipment. The media is heated to a temperature of 37° C.±0.5° C. One weighed capsule is placed in each of the six baskets. In the seventh basket an empty capsule is placed. This is measured as a blank reference. The stirring is started as soon as the baskets are lowered into the vessels. The measured amounts of buffer solution, needed for the changes of pH in the vessels, are preheated to 37° C., before addition to the vessels. When the buffer is to be added, the baskets are elevated from the vessels, the buffer is added, the solution in the vessel is stirred to homogenise the solution and the baskets are lowered into the vessels again. The sample is filtered through a 0.7 μm filter. The absorbances of the filtered samples are measured directly at 290 nm.

Dissolution Method IV for MICAP (Midodrine Hydrochloride Multiple Unit Capsules). HPLC-detection The dissolution parameters are described in Method III. The measurement is performed by HPLC.

| | |
|---|---|
| Column | Spherisorb ODS-1; 5 μm; 25 cm; ID 4.6 μm |
| Injection volume | 20 μl |
| Flowrate | 1.0 ml/min |
| Mobile phase | Phosphate buffer pH 3: methanol 77:23 (v/v) |
| Detection | 290 nm |
| Runtime | 30 min |

Reagents for dissolution are described in Method III.

Buffer solution pH 3 is prepared by dissolving 23.6 g potassium dihydrogen phosphate in 900 ml purified water. o-Phosphoric acid 85% is used to adjust pH. The flask is filled to 1 l.

Standards:

Two stock solutions with a concentration of midodrine hydrochloride 120 μg/ml in 0.01N HCl are prepared. The solutions should be stored in refrigerator.

Prepare from each stock solution two standard solutions with a concentration of midodrine hydrochloride approximately 1.5 μg/ml and 15 μg/ml respectively, diluted with 0.01N HCl. Desglymidodrine hydrochloride is quantified against the standard curve of midodrine hydrochloride. The relative response factor is 1.25 for desglymidodrine hydrochloride to midodrine hydrochloride.

Performance:

The dissolution is performed as described in Method III. The sample is withdrawn with a pipette, transferred to a syringe. The sample is filtered through a 0.7 μm filter. The first ml is returned to the vessel in order to reduce deviation from the desired volume. A sample of approximately 1.5–2 ml is transferred to the vial, the rest is returned to the vessel. The absorbances of the filtered samples are measured as described.

Calculations:

A standard curve is calculated by linear regression, using the standard solutions. The peak area of the sample is the sum of the peak area of midodrine hydrochloride and the peak area of desglymidodrine hydrochloride, where the latter is divided by the relative response factor 1.25.

The results are calculated as % released at any time and presented as a mean value of the six samples together with min and max.

$$\% \text{ dissolved } \frac{A \text{ vol } 100}{b \text{ } x}$$

Where

A sum of peak area of midodrine hydrochloride and desglymidodrine hydrochloride (corr.)

Vol 600 ml for up to 2 hours 730 ml for up to 7.5 hours and 800 ml for up to 12 hours for capsules (MICAP)

100% b slope of the calibration curve (A/mg/ml)

x declared amount (mg)

EXAMPLES

Example 1

Composition Made by Employment of Triple Compression

A tablet was prepared from the following ingredients:

| Core: | |
|---|---|
| Midodrine hydrochloride | 50 mg |
| Klucel MF | 2.0 mg |

-continued

| | |
|---|---|
| Methocel E 50 | 93.0 mg |
| 1st compression layer: | |
| Midodrine hydrochloride | 1.5 mg |
| Klucel MF | 6.6 mg |
| Methocel E 15 | 156.9 mg |
| 2nd compression layer: | |
| Midodrine hydrochloride | 2.8 mg |
| Methocel E 50 | 247.2 mg |

Using the core composition a core weighing 100 mg was compressed using a punch 6 mm in diameter. The core was compression coated using 165 mg of the 1st compression layer composition and a punch of 9 mm in diameter. The thus compression coated core was compression coated again using 250 mg of the 2nd compression layer composition and a punch of 11 mm in diameter.

A composition comprising midodrine hydrochloride 1.2 mg, Methocel E5 9.7 mg and Talc 8.5 mg was applied to the tablet by spray coating.

The following results were obtained with respect to dissolution and release rate (the dissolution method employed throughout the examples and claims is in accordance with the method described in USP and Ph.Eur, method 2 (paddle) employing 0.1 N hydrochloric acid as dissolution medium, 500 ml of dissolution medium, 100 rpm, 37° C. and the amount of midodrine (and/or desglymidodrine) released was measured by UV at at wavelength of 213.4.

% w/w dissolved based on the total weight of the composition tested

| time (hours) | core | core + 1 layer | core + 2 layers | core + 2 layers and coated |
|---|---|---|---|---|
| 0.5 | 14.86 | 4.02 | | 13.30 |
| 1 | | 5.90 | 5.89 | 15.89 |
| 2 | 26.26 | 9.38 | 9.06 | 20.15 |
| 3 | 32.10 | 14.94 | 11.68 | 23.75 |
| 4 | 36.24 | 25.59 | 13.83 | 27.12 |
| 6 | 42.48 | 44.47 | 17.91 | 36.23 |
| 8 | 45.02 | 56.66 | 21.93 | 52.70 |
| 10 | | 63.07 | 33.67 | 70.52 |
| 12 | | | 40.17 | 85.40 |
| 15 | | | 56.02 | 95.67 |
| 18 | | | 76.08 | 96.81 |
| 20 | | | 82.46 | |

The dissolution profiles of the compositions tested are illustrated in FIGS. 6–9 together with the release rate (% w/w dissolved/hour).

Example 2
Composition Made by Employment of Triple Compression

A tablet was prepared from the following ingredients:

| | |
|---|---|
| Core: | |
| Midodrine hydrochloride | 1.66 mg |
| Hydroxypropylmethyl cellulose E 50 | 48.34 mg |
| Croscarmellose sodium | 10.00 mg |
| | 60.00 mg |
| 1st compression layer | |
| Midodrine hydrochloride | 0.62 mg |
| Hydroxypropylmethyl cellulose E 15 | 126.38 |
| Hydroxypropylmethyl cellulose K 100 LV | 8 |
| | 135.00 mg |
| 2nd compression layer | |
| Midodrine hydrochloride | 1.99 mg |
| Hydroxypropylmethyl cellulose E 50 | 143.01 mg |
| | 145.00 mg |

Using the core composition a core weighing 60 mg was compressed using a punch 6 mm in diameter. The core was compression coated using 135 mg of the $1^{st}$ compression layer composition and a punch of 9 mm in diameter. The thus compression coated core was compression coated again using 145 mg of the $2^{nd}$ compression layer composition and a punch of 11 mm in diameter.

A composition comprising midodrine hydrochloride 0.73 mg, hydroxypropylmethyl cellulose E 5 3.58 mg, Talc 2.51 mg and propylene glycol 0.71 mg was applied to the tablet by spray coating.

Finally a top coat comprising hydroxypropylmethyl cellulose E 5 1.79 mg, Talc 1.25 mg and propylene glycol 0.36 mg was applied to the tablet by spray coating.

Figure 17:
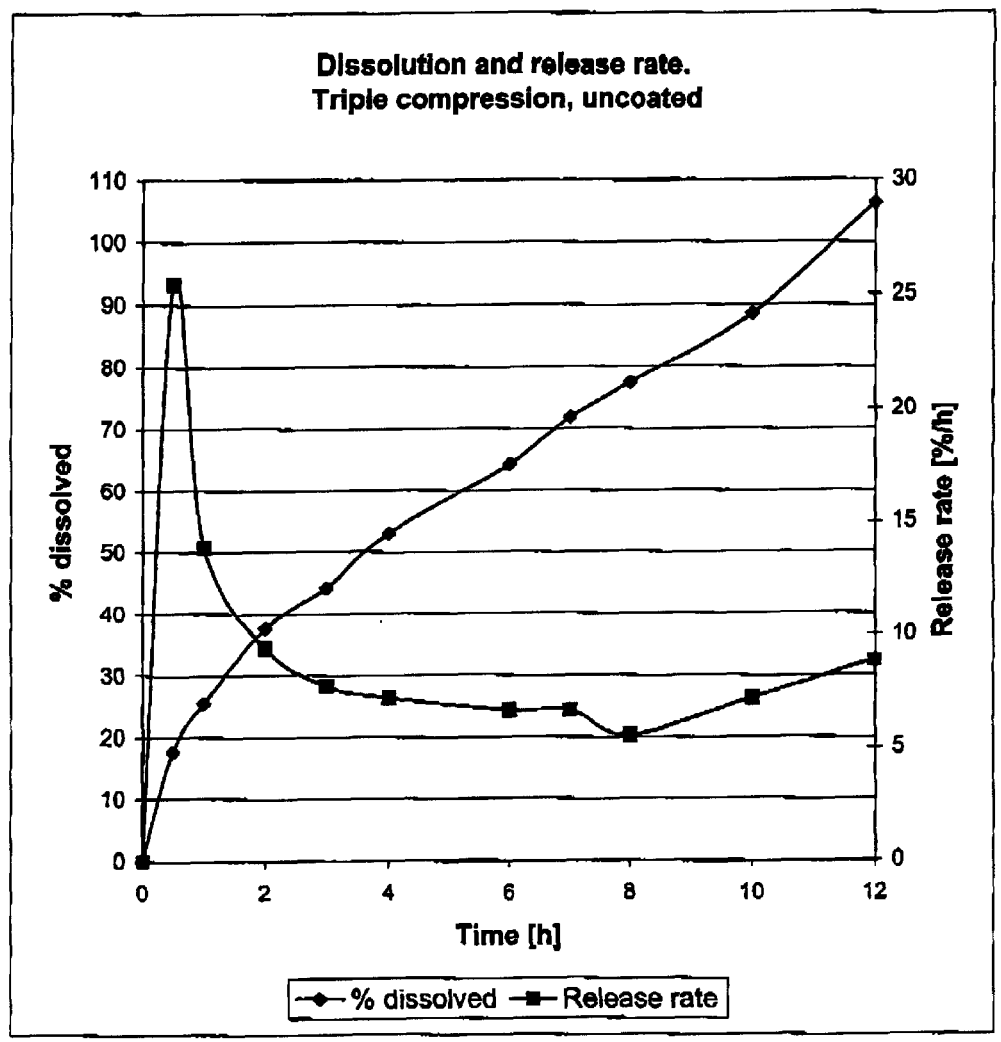
FIGS. 17–18 illustrate the results of Example 2, FIGS. 19 and 20 the results of Example 12.
Figure 18:
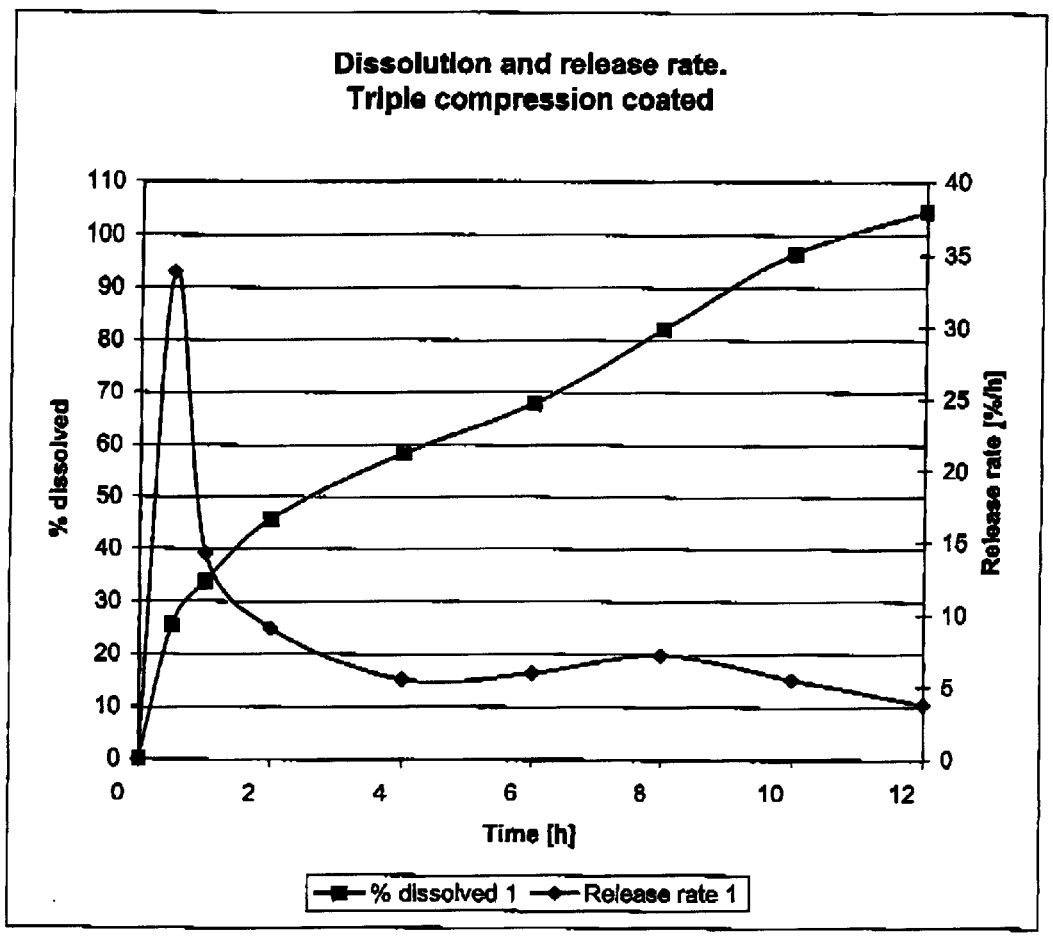

The following results were obtained with respect to dissolution and release rate employing Dissolution Method I. The results are also shown in FIGS. 17 and 18.

% w/w dissolved based on the total weight of the compostion tested

| Time [hours] | Core + $1^{st}$ + $2^{nd}$ compression layer (n = 2) | | Core + $1^{st}$ + $2^{nd}$ compression layer + coating (n = 6)* | |
|---|---|---|---|---|
| | % dissolved | Release rate [%/h] | % dissolved | Release rate [%/h] |
| 0.0 | 0.0 | 0.0 | 0.0 | 0.0 |
| 0.5 | 17.7 | 25.44 | 25.5 | 33.80 |
| 1.0 | 25.4 | 13.83 | 33.8 | 14.25 |
| 2.0 | 37.6 | 9.40 | 45.7 | 9.10 |
| 3.0 | 44.2 | 7.74 | — | — |
| 4.0 | 53.1 | 7.19 | 58.3 | 5.53 |
| 6.0 | 64.2 | 6.64 | 67.8 | 5.95 |
| 7.0 | 71.9 | 6.64 | — | — |
| 8.0 | 77.4 | 5.53 | 82.1 | 7.20 |
| 10.0 | 88.5 | 7.19 | 96.6 | 5.53 |
| 12.0 | 106.2 | 8.85 | 104.2 | 3.80 |

*Data from the release of the product is shown

Example 3
Composition Made as a Coated Matrix

The following compositions were prepared:

| | |
|---|---|
| Composition 1: | |
| Core: | |
| Midodrine hydrochloride | 10.0 mg |
| Klucel LF | 340.0 mg |
| Insoluble inner coat | |
| Methocel E 5 | 0.2 mg |
| Magnesium stearate | 0.1 mg |
| Talc Ponderax | 0.4 mg |
| Anti foam | 4.8 µg |
| Eudragit NE 30 D | 4.5 mg |
| Soluble outer coat | |

-continued

| | |
|---|---|
| Methocel E 5 | 1.8 mg |
| Talc Ponderax | 1.8 mg |

Composition 2:

| | |
|---|---|
| Core: | |
| Midodrine hydrochloride | 10.0 mg |
| Klucel MF | 340.0 mg |
| Insoluble inner coat | |
| Methocel E 5 | 0.2 mg |
| Magnesium stearate | 0.1 mg |
| Talc Ponderax | 0.4 mg |
| Anti foam | 4.8 mg |
| Eudragit NE 30 D | 4.5 mg |
| Soluble outer coat | |
| Methocel E 5 | 1.8 mg |
| Talc ponderax | 1.8 mg |

Cores of both composition 1 and composition 2 were compressed using a punch 10 mm in diameter. Core weighing 350 mg.

Both types of cores were coated with an insoluble inner coat and a soluble outercout. The release profile can be shifted up or down by changing the amount of weight increase of cores when applying the inner coat.

If suitable, the release profile can be changed by coating with other acrylic resins such as Eudragit RL 30 D, Eudragit RS 30 D or combinations thereof, or using other types of film forming agents such as ethylcellulose or silicone polymers. Furthermore, the release profile can be changed by using other types of matrix former such as acrylic resins, other types of cellulose ethers such as L-HPC (low-substituted hydroxypropylcellulose), HPC (hydroxypropylcellulose), HPMC (hydroxypropylmethylcellulose), HEC (hydroxyethylcellulose), MC (methylcellulose), HEMC (hydroxyethylmethylcellulose), EC (ethylcellulose) or other viscosity grades of HPC (hydroxypropylcellulose).

The following results were obtained with respect to dissolution and release rate (performed in accordance with the general method described herein).

% w/w dissolved based on the total weight of the composition tested

| time (hours) | comp. 1 | comp. 1 coated | comp. 2 | comp. 2 coated |
|---|---|---|---|---|
| 1 | 16.72 | 7.67 | 15.77 | 6.41 |
| 2 | 27.25 | 14.60 | 22.36 | 10.85 |
| 3 | 36.86 | 21.24 | | |
| 4 | 45.66 | 27.59 | 32.14 | 19.62 |
| 6 | 60.37 | 38.18 | 36.26* | 24.03* |
| 8 | | 49.10 | 49.13* | 38.74* |
| 10 | 80.74 | 59.82 | | |
| 12 | 87.09 | 69.74 | 54.44* | 44.83* |
| 15 | 91.37 | 81.48 | 63.06 | 54.89 |
| 18 | | | 66.70* | 59.27* |

*Time is 5, 9, 11 and 17 hours

The results are also shown in FIGS. 10–13.

Example 4
Multilayer Coating Compositions

The following compositions were prepared:

Composition 1:

| | |
|---|---|
| Core (Non pareil) | 200 mg |
| 1. coat | |
| Midodrine | 4.0 mg |
| Methocel E 5 M | 0.3 mg |
| Magnesium Stearate | 60.0 μg |
| Talc ponderax | 0.5 mg |
| Anti foam | 4.0 μg |
| Eudragit NE 30 D | 5.2 mg |
| 2. coat | |
| Midodrine | 3.0 mg |
| Methocel E 5 M | 0.3 mg |
| Magnesium Stearate | 60.0 μg |
| Talc ponderax | 0.5 mg |
| Anti foam | 4.0 μg |
| Eudragit NE 30 D | 6.1 mg |
| 3. coat | |
| Midodrine | 2.0 mg |
| Methocel E 5 M | 0.3 mg |
| Magnesium Stearate | 80.0 μg |
| Talc ponderex | 0.6 mg |
| Anti foam | 6.0 μg |
| Eudragit NE 30 D | 7.1 mg |
| 4. coat | |
| Midodrine | 1.0 mg |
| Methocel E 5 M | 0.4 mg |
| Magnesium Stearate | 80.0 μg |
| Talc ponderax | 0.7 mg |
| Anti foam | 6.0 μg |
| Eudragit NE 30 D | 7.8 mg |
| Outer coat | |
| Methocel E 5 | 1.0 mg |
| Talc ponderax | 1.0 mg |

Non-pareil beads were coated in four steps with four different films in a fluid bed coater.
1. film comprising 1. coat
2. film comprising 2. coat
3. film comprising 3. coat
4. film comprising 4. cost.

A final layer of coating comprising the outer coat was applied and the films were cured at 70° C.

| | | |
|---|---|---|
| Composition 2: | Core (Non pareil) | 200 mg |

Non-pareil beads were coated in seven steps with four different films alternating with a blank film in a fluid bed coater.

The four different film formulations are similar to the four different film formulations in composition 1, the alternating coats are as follows:

| | |
|---|---|
| Alternating coat | |
| Methocel E 5 M | 0.2 mg |
| Magnesium stearate | 40.0 μg |
| Talc ponderax | 0.3 mg |
| Anti foam | 2.0 μg |
| Eudragit NE 30 D | 3.5 μg |

1. film comprising 1. coat
2. film comprising Alternating coat
3. film comprising 2. coat
4. film comprising Alternating coat
5. film comprising 3. coat
6. film comprising Alternating coat
7. film comprising 4. coat A final layer of coating comprising outer coat in composition 1 was applied and the films were cured at 70° C.

| Composition 3: | |
|---|---|
| Core (Non pareil) | 200 mg |
| 1. coat | |
| Midodrine | 4.0 mg |
| Paraffin, solid | 0.3 mg |
| Acetyltributyl citrate | 0.1 mg |
| Ethylcellulose | 1.9 mg |
| Aerosil 200 | 28.0 μg |
| 2. coat | |
| Midodrine | 3.0 mg |
| Paraffin, solid | 0.3 mg |
| Acetyltributyl citrate | 0.1 mg |
| Ethylcellulose | 2.2 mg |
| Aerosil 200 | 32.0 μg |
| 3. coat | |
| Midodrine | 2.0 mg |
| Paraffin, solid | 0.4 mg |
| Acetyltributyl citrate | 0.1 mg |
| Ethylcellulose | 2.5 mg |
| Aerosil 200 | 40.0 μg |
| 4. coat | |
| Midodrine | 1.0 mg |
| Paraffin, solid | 0.4 mg |
| Acetyltributyl citrate | 0.2 mg |
| Ethylcellulose | 2.8 mg |
| Aerosil 200 | 40.0 μg |
| Outer coats | |
| Paraffin, solid | 0.5 mg |
| Acetyltributyl citrate | 0.2 mg |
| Ethylcellulose | 3.3 mg |
| Aerosil 200 | 50.0 μg |

Non-pareil beads were coated in four steps with four different films in a fluid bed coater:
1. film comprising 1. coat
2. film comprising 2. coat
3. film comprising 3. coat
4. film comprising 4. coat.

A final layer of coating comprising outer coats was applied.

Figure 14:
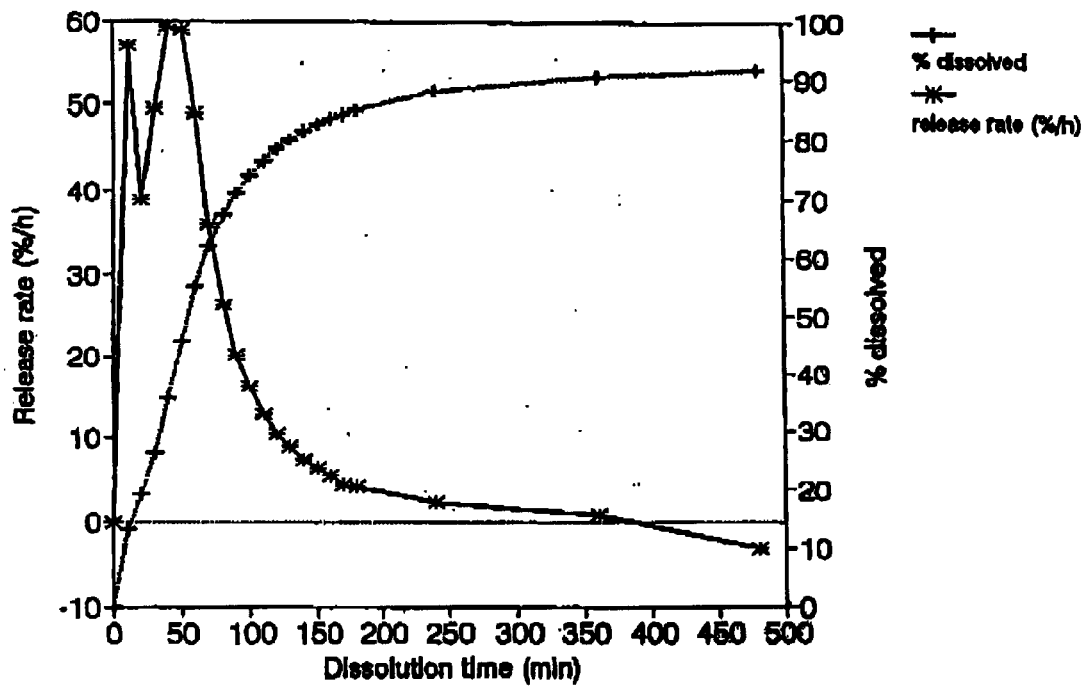
FIGS. 14–16 illustrate the results of Example 4.
Figure 15:
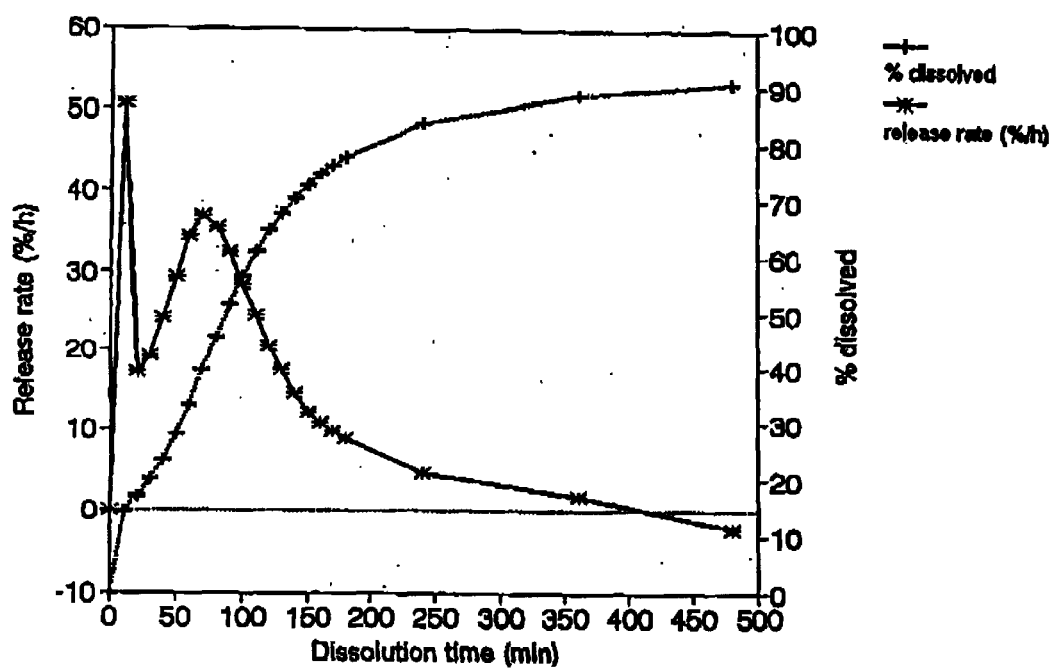
Figure 16:
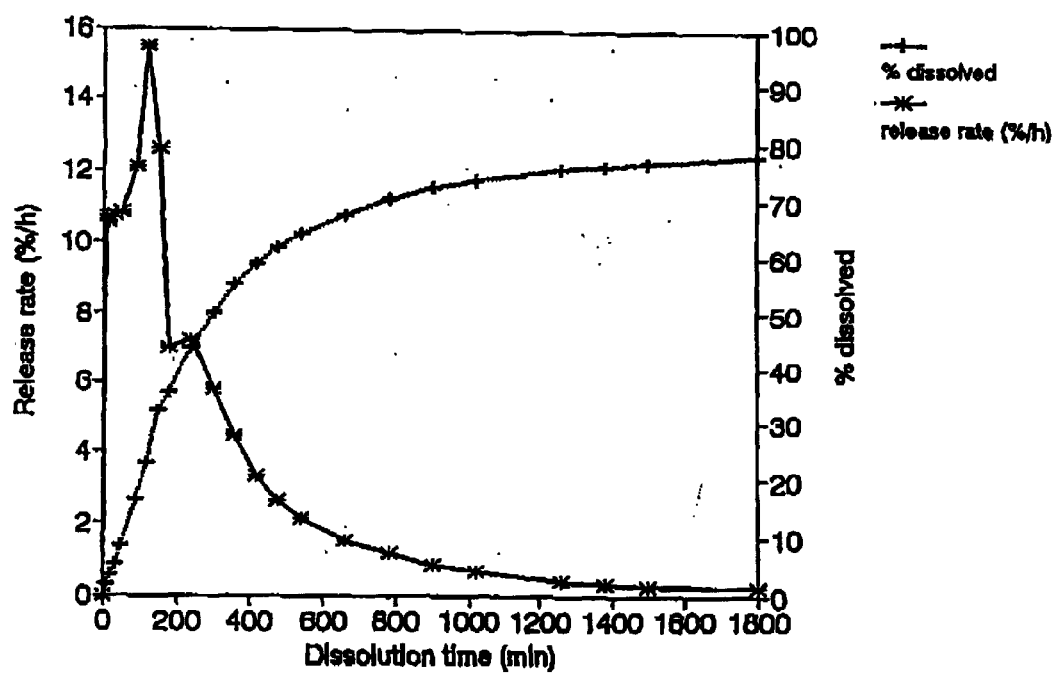

The following results were obtained with respect to dissolution and release rate (performed in accordance with the general method described herein). The results are also shown in FIGS. 14–16.

| % w/w dissolved based on the total weight of the composition tested | | | |
|---|---|---|---|
| time (hours) | composition 1 | composition 2 | composition 3 |
| 0.5 | 26.02 | 19.84 | 5.41 |
| 1 | 55.24 | 33.08 | |
| 2 | 78.38 | 64.39 | 22.92 |
| 3 | 85.01 | 77.64 | 35.52 |
| 4 | 87.91 | 83.41 | 43.61 |
| 6 | 90.43 | 88.39 | 55.16 |
| 8 | 91.61 | 90.63 | 61.75 |
| 15 | | | 72.09 |

If suitable, the release profile can be changed by coating with other acrylic resins such as Eudragit RL 30 D, Eudragit RS 30 D or combinations thereof, or using other types of film forming agents such as ethylcellulose or silicone polymers, or incorporating lipophilic compounds such as, e.g., stearic acid, capric acid or hydrogenated Castor oil in the film.

Example 5

Preparation of a Controlled Release Composition Using Commercially Available Filmforming Agents The present example illustrates the preparation of a coated pellet composition. The aim was to prepare pellets having a release kinetic different from zero order release.

Pellets were prepared from the following ingredients:

| I | Midodrine hydrochloride | 600.0 g |
|---|---|---|
| II | Microcrystalline cellulose (Type PH 101) | 752.0 g |
| III | Lactose monohydrate | 2608.0 g |
| IV | Sodium carboxymethylcellulose | 40.0 g |
| V | Purified water | 1120.0 g |

I+II+III+IV are admixed in a Fielder intensive mixer at an appropiate time and mixing intensity.

V is applied to the mixture (I–IV) while mixing. When V is applied the mixing is continued at an appropiate time with an appropiate mixing intensity.

The wetted mass is extruded through a screen with apertures between 0.4–1.0 mm.

The extrudate is spheronised until the surface of the resulting pellets is smooth.

An inner and an outer coating were applied:
Inner coat
The weight of the pellets is increased with 8.5% w/w.

| I | Hydroxypropylmethylcellulose | 13.5 g |
|---|---|---|
| II | Magnesium stearate | 2.9 g |
| II | Talc | 25.2 g |
| IV | Eudragit NE 30 D | 895.1 g |
| V | Purified water | 1136.4 g |

The pellets are coated in a fluid bed with appropriate process parameters.

Immediately after the inner coat has been applied an outer coat is applied.
Outer Coat
The weight of the pellets is increased with 1% w/w.

| I | Hydroxypropylmethylcellulose | 20.0 g |
|---|---|---|
| II | Talc | 20.0 g |
| III | Purified water | 460.0 g |

The pellets are coated in a fluid bed with appropriate process parameters.

The weight of 1 unit dose containing 30 mg midodrine hydrochloride is 219 mg.

The release profile can be shifted up or down by changing the amount of weight increase of pellets when applying the inner coat.

The release profile can be changed by mixing fractions of pellets with different amounts of inner coating applied or the release profile can be changed by coating with other acrylic resins such as Eudragit RL 30 D, Eudragit RS 30 D or combinations thereof, or using other types of film forming agents such as ethylcellulose or silicone polymers.

Furthermore, the release profile can be changed by applying a fraction of non-coated pellets or by applying an anteric coating to a fraction of pellets.

Example 6

Preparation of a Controlled Release Formulation Using a Film Containing Paraffin The present example illustrates the preparation of a coated pellet composition. The aim was to prepare pellets having a release kinetic different from zero order release.

Coated pellets were prepared from the following ingredients:

The composition and manufacturing process of pellets are similar to Example 5.

A coating was applied. Paraffin-containing film; the weight of the pellets is increased with 6% w/w.

| I | Paraffin, solid | 29.89 g |
| II | Acetyltributyl citrate | 10.53 g |
| III | Ethyl cellulose | 196.61 g |
| IV | Silicium dioxide (Aerosil 200) | 2.95 g |
| V | Isopropyl alcohol | 3970.03 g |

The pellets are coated in a fluid bed with appropriate process parameters.

The weight of 1 unit dose containing 30 mg midodrine hydrochloride is 212 mg.

Example 7

Preparation of a Controlled Release Composition Having a Zero Order Release

The present example illustrates the preparation of a coated beads composition. The aim was to prepare beads having a zero order release kinetic.

Coated beads were prepared from the following ingredients:

Non dissolvable nonpareil beads of equal size are coated with a suspension of midodrine hydrochloride. A diffusion barrier is coated on top of the midodrine hydrochloride layer, and thereby controlling the release of midodrine hydrochloride.

4000 g non-parell beads having a uniform particle size in a range between 0.4 mm and 1.0 mm are transferred to a fluid bed coater.

The beads are coated with coating suspension 1 (containing midodrine hydrochloride):

| I | Hydroxypropylmethylcellulose | 8.8 g |
| II | Magnesium stearate | 1.9 g |
| III | Talc | 16.5 g |
| IV | Eudragit NE 30 D | 585.1 g |
| V | Purified water | 742.1 g |
| VI | Midodrine hydrochloride | 200.0 g |

The weight of the beads is increased with 10% w/w.

The beads are coated employing appropriate process parameters.

Immediately after coating suspension 1 has been applied a second coating suspension is applied.

The beads are coated with coating suspension 2:

| I | Hydroxypropylmethylcellulose | 11.7 g |
| II | Magnesium stearate | 2.5 g |
| III | Talc | 21.7 g |
| IV | Eudragit NE 30 D | 772.3 g |
| V | Purified water | 979.6 g |

The weight of the coated beads is increased with 6% w/w.

The pellets are coated employing appropriate process parameters.

Immediately after coating suspension 2 has been applied a third coating suspension is applied.

The beads are coated with coating solution 3:

| I | Hydroxypropylmethylcellulose | 23.3 g |
| II | Talc | 23.3 g |
| III | Purified water | 536.8 g |

The weight of the coated beads is increased with 1% w/w.

The beads are coated in a fluid bed employing appropriate process parameters.

The weight of 1 unit dose containing 20 mg midodrine hydrochloride is 471 mg.

By changing the weight gain of the beads when applying the second coating suspension, the release profile can be shifted up or down.

The release profile can be changed by mixing fractions of beads having different amounts of second coating suspension applied or the release profile can be changed by coating with other acrylic resins such as Pudraga RL 30 D, Eudragit RS 30 D or combinations thereof, or using other types of film forming agents such as ethylcellulose or silicone polymers.

The above mentioned filmforming agents can also be combined with pore forming agents such as cellulose ethers, polyoles, PEG's.

Furthermore, the release profile can be changed by applying an enteric coating to a fraction of the coated beads.

Example 8

Preparation of a Zero Order Controlled Release Composition

The present example illustrates the preparation of a coated minitablet composition. The aim was to prepare coated minitablets of equal size in order to obtain a zero order release kinetic.

Formulation of minitablets:

| I | Midodrine hydrochloride | 800.0 g |
| II | Dicalcium phosphate | 2960.0 g |
| III | Talc | 100.0 g |
| IV | Magnesium stearate | 40.0 g |
| V | Polyvinylpyrrolidone 90 | 100.0 g |
| VI | Purified water | 800.0 g |

V is dissolved in VI.

I+II are transferred to a Fielder intensive mixer and admixed at an appropiate time and mixing intensity.

The mixture is wetted with the solution V+VI.

Granulation is performed at an appropriate time and mixing intensity.

The drying of the wet granulate is carried out in an Aeramatic fluid bed.

The dried granulate is passed through a suitable sieve. IV+V are sieved through a 0.3 mm sieve and admixed to the sieved particulate mixture in a cube mixer for 10 min.

The thus obtained particulate mixture is compressed into tablets weighing 15 mg.

A dose of 30 mg midodrine corresponds to 10 minitablets.

Coating of the minitablets:

The minitablets are coated with inner and outer coatings corresponding to the description in Example 7.

By changing the weight gain of the minitablets when applying the inner coat, the release profile can be shifted up or down.

The release profile can be changed by mixing fractions of minitablets having different amounts of inner coating applied or the release profile can be changed by coating with other acrylic resin such as Eudragit RL 30 D, Eudragit RS 30 D or combinations thereof, or using other types of film forming agents such as ethylcellulose or silicone polymers.

The above mentioned filmforming agents can also be combined with pore forming agents such as, e.g., cellulose ethers, polyoles, PEG's, etc.

Furthermore, the release profile can be changed by applying an enteric coating to a fraction of the coated minitablets.

Example 9

Preparation of a Controlled Release Composition Having a Release Kinetic Different From That of Zero Order Matrix minitablets:

| I | Midodrine hydrochloride | 800.0 g |
|---|---|---|
| II | Ethyl cellulose (10 μm) | 2960.0 g |
| III | Talc | 200.0 g |
| IV | Magnesium stearate | 40.0 g |
| V | Purified water | 800.0 g |

I+II are admixed in a Fielder intensive mixer at an appropriate time and mixing intensity.

The mixture is wetted with V while mixing at an appropriate mixing intensity.

The wetted mixture is granulated at an appropriate time and mixing intensity.

The drying of the wet granulate is carried out in an Aeramatic fluid bed.

The dried granulate is passed through a suitable sieve. III+IV are sieved through a 0.3 mm sieve and admixed to the sieved particulate mixture in a cube mixer for 10 min.

The thus obtained particulate mixture is compressed into tablets weighing 15 mg.

A dose of 30 mg of midodrine hydrochloride is contained in 10 minitablets.

If suitable, the release profile can be changed by using other cellulose ethers such as HPC, L-HPC, HPMC or combinations of thereof.

The principle of a matrix composition may also be used for a single unit tablet containing the total amount of midodrine hydrochloride in one unit.

In order to further increase the retardation of the dissolution of midodrine hydrochloride the minitablets may be coated according to Example 7. The amount of coating applied may be varied to shift the dissolution profile up or down.

Example 10

Preparation of a Controlled Release Composition Having Release Kinetic Different Form Zero Order Matrix minitablets:

| I | Midodrine hydrochloride | 800.0 g |
|---|---|---|
| II | Ethyl cellulose (10 μm) | 2960.0 g |
| III | Talc | 200.0 g |
| IV | Magnesium stearate | 40.0 g |
| V | Isopropyl alcohol | 800.0 g |

I+II are admixed in a Fielder intensive mixer at an appropriate time and mixing intensity.

The mixture is wetted with V while mixing at an appropriate mixing intensity.

The wetted mixture is granulated for an appropriate time and mixing intensity.

The drying of the wet granulate is carried out in an Aeramatic fluid bed.

The dried granulate is passed through a suitable sieve. III+IV are sieved through a 0.3 mm sieve and admixed to the sieved particulate mixture in a cube mixer for 10 min.

The thus obtained particulate mixture is compressed into tablets weighing 15 mg.

A dose of 30 mg of midodrine hydrochloride is contained in 10 minitablets.

In order to further increase the retardation of the dissolution of midodrine hydrochloride the minitablets may be coated according to Example 7. The amount of coating applied may be varied to shift the dissolution profile up or down.

Example 11

Composition Made by Employment of Double Compression

A tablet was prepared from the following ingredients.

| 1$^{st}$ compression layer | Midodrine hydrochloride | 2.40 g |
|---|---|---|
| | Starch 1500 | 89.46 g |
| | Lactose monohydrate | 180.00 g |
| | Eudragite RS 30 D | 75.0 g |
| | Acetyl tributylcitrate | 5.64 g |
| 2$^{nd}$ compression layer | Midodrine hydrochloride | 0.5 g |
| | Hydroxypropylmethyl-cellulose E 50 | 49.5 g |

The granulate for 1$^{st}$ compression layer was prepared in the following way:

Midodrine hydrochloride and Starch 1500 was mixed by hand. This mixture and lactose monohydrate was mixed in a Moulinex food processor for 30 sec.

The granulating fluid comprising Eudragit RS 30 D and acetyl tributylcitrate was mixed by stirring for 5 min.

The granulating fluid was applied to the powder mixture while mixing in the Moulinex food processor. The time for applying the granulating fluid was 45 sec.

Wet massing time for the moist powder mixture was 30 sec.

The moist granulate was tray dried and the dried granulate was passed through a 1000 μm screen.

The granulate for 2$^{nd}$ compression layer was prepared in the following way:

Midodrine hydrochloride and hydroxypropylmethyl cellulose E 50 was mixed by hand and finally passed through a 500 μm screen.

A double compression tablet was prepared in the following way:

A shallow concave round punch 11 mm in diameter was used to compress the tablet. 250 mg of the granulate for $1^{st}$ compression layer was weighed into the die and compressed gently to a loose compact. 200 mg of the granulate for $2^{nd}$ compression layer was weighed on top the loose compact. The loose compact and the granulate for $2^{nd}$ compression layer was compressed with a force of approx. 17 kN to form a coherent tablet.

After compression a release controlling film, a film containing midodrine hydrochloride and a blank film were applied to the tablets.

Example 12

Composition Made in the Form of Capsules Containing Multiple Units (MICAP)—EC Pellets Coated With 45% w/w Dry Matter The midodrine controlled release product is prepared by manufacturing one type of pellet, which afterwards is coated with different types of film coatings. The capsule ends up with 3 different types of pellets (one non-coated pellet, one CR-coated pellet and one EC-pellet).

Pellets Preparation

The pellet is prepared by the use of an extrusion/spheronization technique. The ingredients are listed in Scheme 12-1.

Scheme 12-1:

| Ingredients | Amount (g) pr. Batchsize |
|---|---|
| Microcrystalline cellulose | 2135.0 |
| Lactose monohydrate | 1207.5 |
| Carmellose Sodium | 70.0 |
| Midodrine Hydrochloride | 87.5 |
| Purified water | 2000.0 |

The ingredients are mixed and wetted in a Fielder high shear mixer in which the water is applied by a nozzle.

The wetted mass was extruded in a Nica E 140 extruder with a screen size of 600 μm (those pellets which is being used for non coated pellets and for CR-coating) or 800 μm (those pellets used for EC-coating). The extrudate was spheronized in a laboratory unit for 5 min. The pellets were dried in a laboratory scala fluid bed for approx. 75 min at 50° C.

The dried pellets used for non coated pellets and for CR-coating were screened through a screen of 700 μm and the dried pellets used for EC-coating were fractionated with a lower screen of 500 μm and a upper screen of 1000 μm.

Step 1 Pellets (Non Coated Pellets)

One batch of these pellets is not coated because it is used as an immediate release unit. The pellets are a part of the content in the capsule.

Step 2 Pellets (CR-coated Pellets)

One batch of these pellets is coated with an inner coat and an outer coat in a fluid bed (GPCG3) with a 0.8 mm spray nozzle and a spray pressure of 2.5 bar. The composition for the coating is shown in Scheme 12-2.

Scheme 12-2:

| Ingredients | Amount (g) pr. batchsize |
|---|---|
| Inner coat (batchsize 2000 g) | |
| Hypromellose (viscosity 5 cps) | 13.1 |
| Purified water | 1094.0 |
| Magnesium stearate | 2.7 |
| Talc | 26.2 |
| Polyacrylate dispersion 30% (Eudragit NE30D) | 864.0 |
| Outer coat (batchsize 1000 g) | |
| Hypromellose (viscosity 5 cps) | 40.0 |
| Purified water | 920.0 |
| Talc | 40.0 |

In the coating process the following amount of inner and outer coat were applied. The amount of dry matter applied calculated in percentage of the core weight also appears from below.

Inner coat: 1788.1 g per 3000.0 g pellets (dry matter: 9% of the core weight)

Outer coat: 375.0 g per 3000.0 g pellets (dry matter: 1% of the core weight)

Throughout the coating process the bed temperature was maintained substantially in the interval from 20–25° C. by adjustment of the liquid flow rate or the inlet temperature. The inlet air temperature was kept at approximately 32° C. After the application of the coatings the coated pellets were cured at a bed temperature of approximately 70° C. for 30 min. Then the pellets were screened through a screen 1.0 mm. Oversized material was discarded.

Step 3 Pellets (EC Pellets)

One batch of these pellets is coated with an EC-coat in a fluid bed (Würster technique) with a 0.8 mm spray nozzle and a spray pressure of 2.5 bar. The composition for the coating is shown in Scheme 12-3.

Scheme 12-3:

| Ingredients | Amount (g) pr. batchsize |
|---|---|
| Isopropyl alcohol | 3852.0 |
| Talc | 100.0 |
| Acetyltributyl citrate | 99.2 |
| Methacrylic acid - methyl methacrylate copolymer (1:2) (Eudregit S12.5) | 3948.8 |

In the coating process the following amount of the coat were applied. The amount of dry matter applied calculated in percentage of the core weight also appears from below.

15,517.2 g per 3000.0 g pellets (dry matter: 45% of the core weight)

Throughout the coating process the bed temperature was maintained substantially in the interval from 30–38° C. by adjustment of the liquid flow rate or the inlet temperature. The inlet air temperature was kept at approximately 49° C. After the application of the coating the pellets were screened through a screen 1.3 mm. Oversized material was discarded.

Capsule Filling

The 3 different pellets (steps 1, 2 and 3) were filled into capsules by hand. The amount of pellets per capsule is shown in Scheme 12-4.

Scheme 12-4:

| Unit | Amount (mg) per capsule |
|---|---|
| Capsule | approx. 76.3 |
| Pellets step 1 | approx. 50.4 corresp. to 1.25 mg midrodrine hydrochloride |
| Pellets step 2 | approx. 110.6 corresp. to 2.5 mg midrodrine hydrochloride |
| Pellets step 3 | approx. 72.7 corresp. to .25 mg midrodrine hydrochloride |
| Total weight of capsule | approx. 310 corresp. to 5.0 mg midrodrine hydrochloride |

Dissolution Data

The following results were obtained with respect to dissolution and release rate employing Dissolution Method III The mixture of the 3 types of pellets had the dissolution data shown in Scheme 12-5;

Scheme 12-5

| | Capsule (n = 12) | |
|---|---|---|
| Time (hours) | % dissolved | Release rate (%/h) |
| 0.0 | 0.0 | 0.00 |
| 0.5 | 29.9 | 33.26 |
| 1 | 33.3 | 6.63 |
| 2 | 39.8 | 7.00 |
| 3 | 47.3 | 7.84 |
| 4 | 55.5 | 8.31 |
| 6 | 72.3 | 7.02 |
| 7 | 77.9 | 10.00 |
| 8 | 92.3 | 7.92 |
| 10 | 95.2 | 1.30 |
| 12 | 97.5 | 1.15 |

Figure 19:
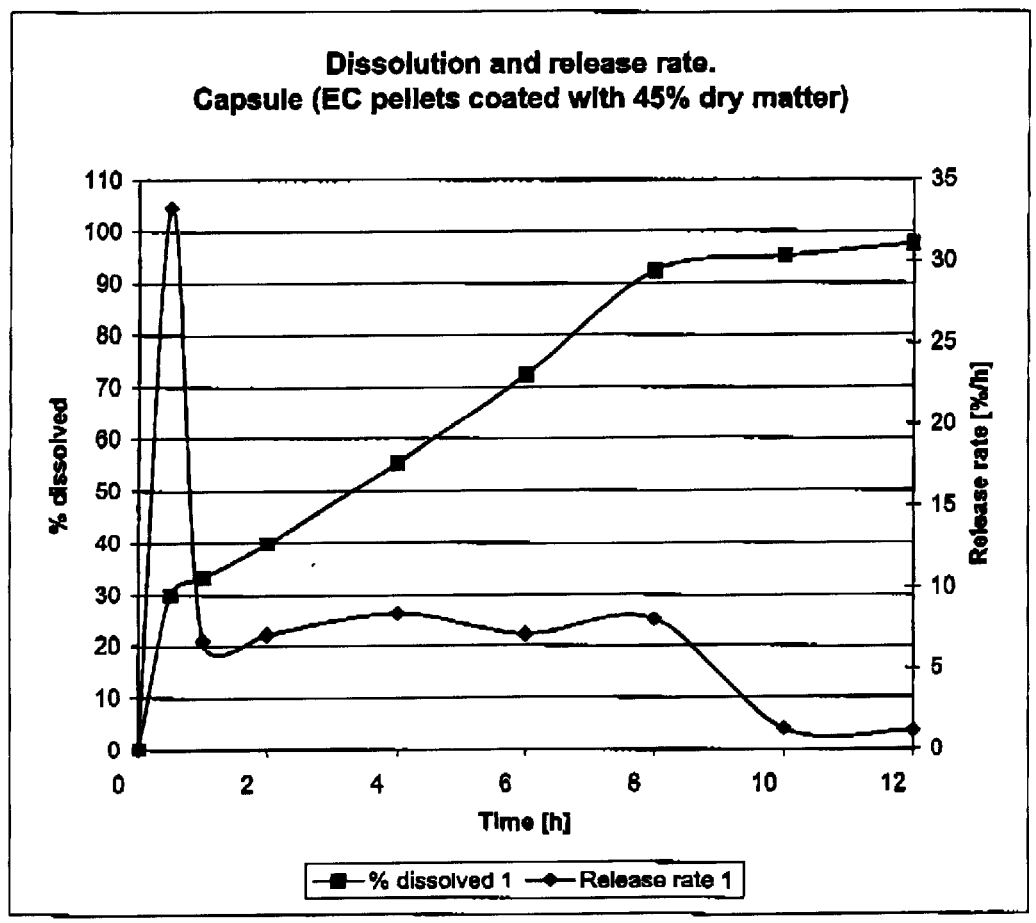

The results are also shown in FIG. 19.

Figure 20:
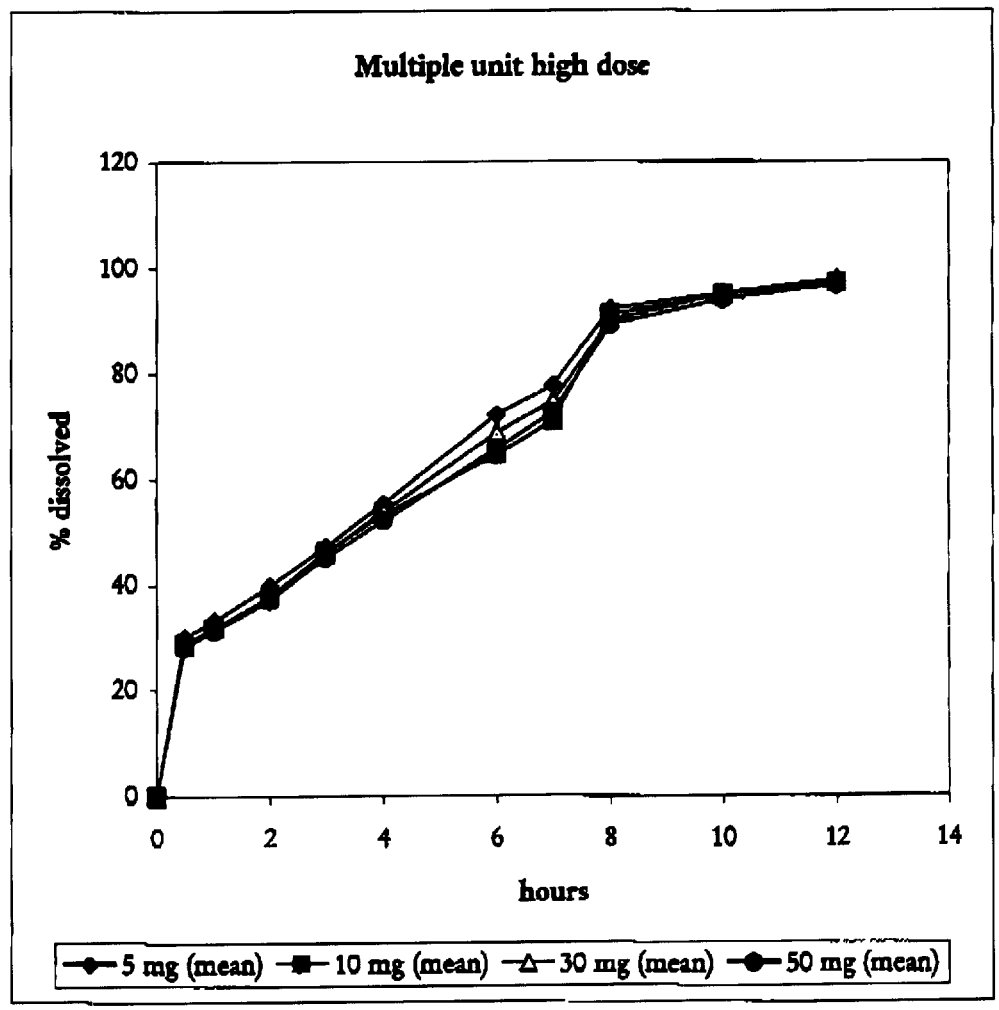

In FIG. 20 is given the dissolution data for 4 different compositions having different content of midodrine hydrochloride. As is evident from the profiles, the dissolution is independent on the midodrine dose.

Example 13

Composition in the Form of Capsules Containing Multiple Units (MICAP)—EC Pellets Coated With 35% w/w Dry Matter The following example illustrates that the amount of dry matter in the EC coating is very important in order to achieve a composition, which has the dissolution characteristics according to the requirements described herein. Thus, an EC coat containing 35% w/w dry matter is apparently not as suitable as an EC coat with 45% w/w dry mater (Example 12).

The midodrine controlled release product is prepared as in Example 12. The only difference is the amount of dry matter applied on the enteric coated pellets.

Pellets Preparation
As described in Example 12
Step 1 Pellets (Non Coated Pellets)
As described in Example 12
Step 2 Pellets (CR-coated Pellets)
As described in Example 12
Step 3 Pellets (EC Pellets)
The composition for the coating and the coating procedure are the same as those being used in Example 12 (except the amount of dry matter applied on the pellets).

In the coating process the following amount of the coat were applied. The amount of dry matter applied calculated in percentage of the core weight also appears from below.

12,069.0 g per 3000.0 g pellets (dry matter: 35% of the core weight)

Capsule Filling

The amount of pellets per test is shown in Scheme 13-1
Scheme 13-1:

| Unit | Amount (mg) per capsule |
|---|---|
| Pellets step 1 | approx. 50.4 corresponding to 1.25 mg midodrine hydrochloride |
| Pellets step 2 | approx. 110.6 corresponding to 2.5 mg midodrine hydrochloride |
| Pellets step 3 | approx. 67.5 corresponding to 1.25 mg midodrine hydrochloride |

Dissolution Data

The following results were obtained with respect to dissolution and release rate employing Dissolution Method III.

The mixture of the 3 types of pellets had the dissolution data shown in Scheme 13-2.

Scheme 13-2

| | Capsule (n = 6) | |
|---|---|---|
| Time (hours) | % dissolved | Release rate (%/h) |
| 0.0 | 0.0 | 0.00 |
| 0.5 | 28..9 | 32.00 |
| 1 | 32.0 | 6.09 |
| 2 | 37.9 | 8.98 |
| 3 | 50.0 | 16.08 |
| 4 | 70.0 | 14.94 |
| 6 | 89.7 | 5.30 |
| 7 | 90.4 | 2.14 |
| 8 | 94.0 | 2.56 |
| 10 | 97.2 | 1.50 |
| 12 | 100.0 | 1.40 |

Figure 21:
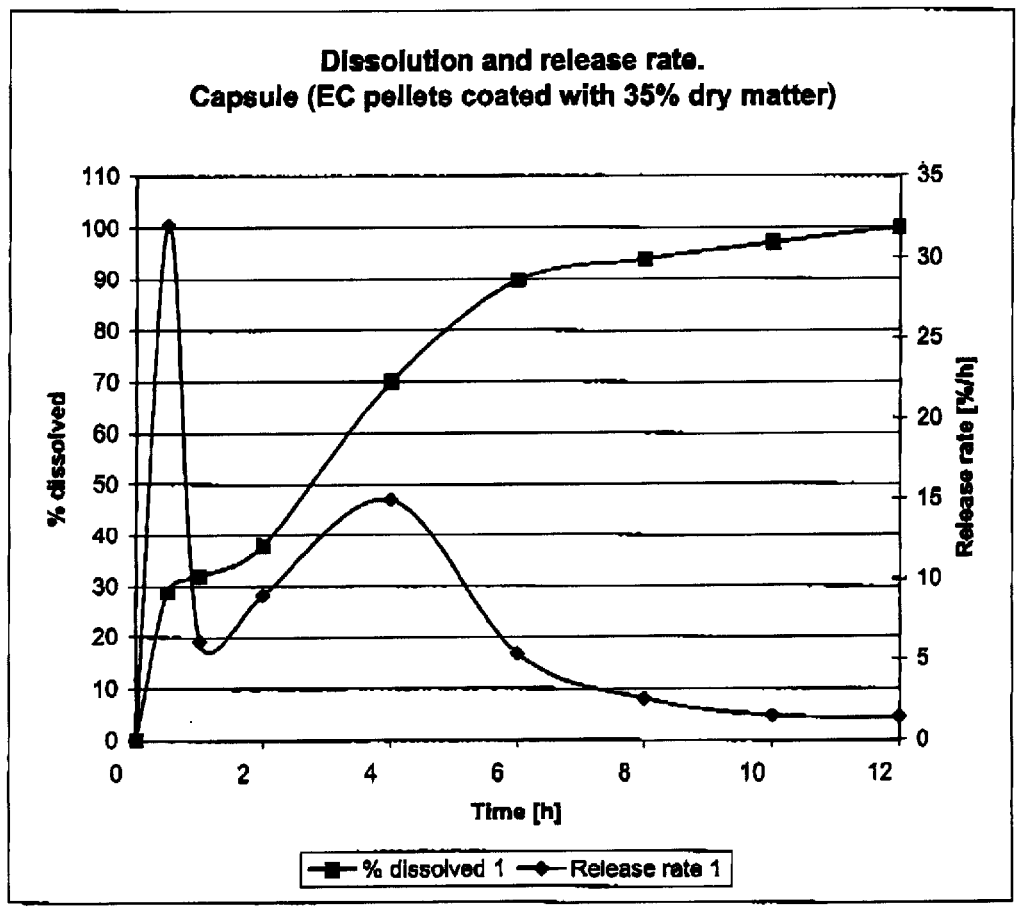
FIG. 21 illustrates the results of Example 13.

The results are also shown in FIG. 21.

Example 14

Composition Made by Employment of Mixing a Matrix Granulate and a Slow Release Granulate The compositions of the granulates are equal to granulates in Example 11.

250 mg of the granulate called $1^{st}$ compression layer (slow release granulate) was mixed with 200 mg of the granulate called $2^{nd}$ compression layer (matrix granulate).

A shallow concave round punch 11 mm in diameter was used to compress the tablet. The granulate mixture was placed in the die and the granulate was compressed with a compression force of approx. 17 kN to form a coherent tablet.

After compression a release controlling film, a film containing midodrine hydrochloride and a blank film were applied to the tablets.

The film compositions and the applied amounts are equal the compositions and amounts applied in Example 11.

The following results were obtained with respect to dissolution and release rate employing Dissolution method I.

| Time [hours] | Tablet 1 (n = 1) | | Tablet 2 (n = 1) | |
|---|---|---|---|---|
| | % dissolved | Release rate [%] | % dissolved | Release rate [%] |
| 0.0 | 0 | 0.0 | 0 | 0.0 |
| 0.5 | 18 | 18.0 | 18 | 18.0 |
| 1.0 | 18 | 0.5 | 18 | 1.0 |
| 2.0 | 19 | 2.0 | 20 | 2.0 |
| 3.0 | 22 | 3.5 | 22 | 2.5 |
| 4.0 | 26 | 5.5 | 25 | 6.5 |
| 6.0 | 48 | 27.0 | 42 | 17.0 |
| 7.0 | 87 | 23.5 | 69 | 19.0 |
| 8.0 | 95 | 4.0 | 80 | 8.0 |
| 10.0 | 96 | 0.5 | 89 | 2.5 |
| 12.0 | 96 | 0.0 | 93 | 2.0 |

% w/w dissolved based on the total weight of the compostion tested

Figure 22:
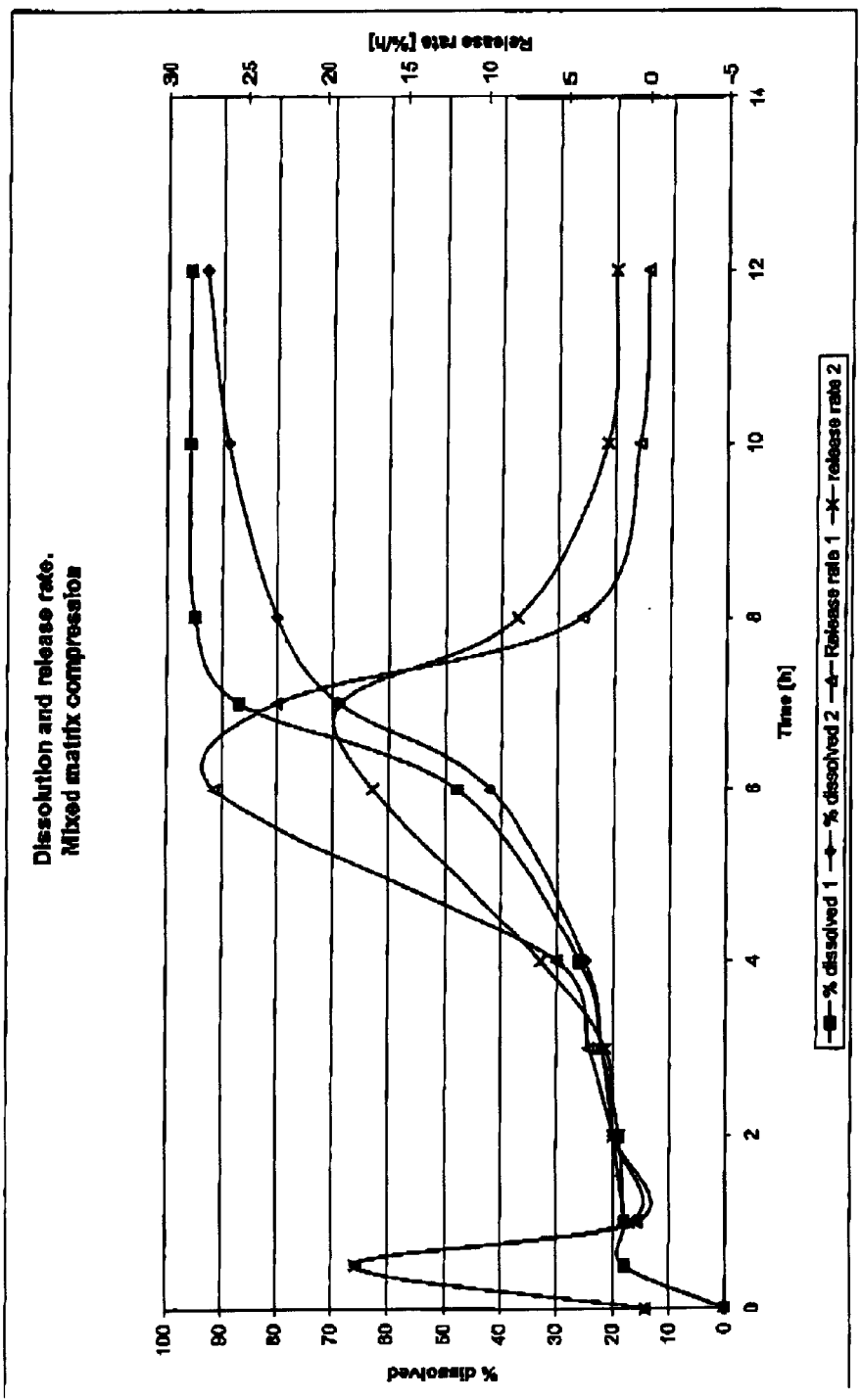
Figure 23:
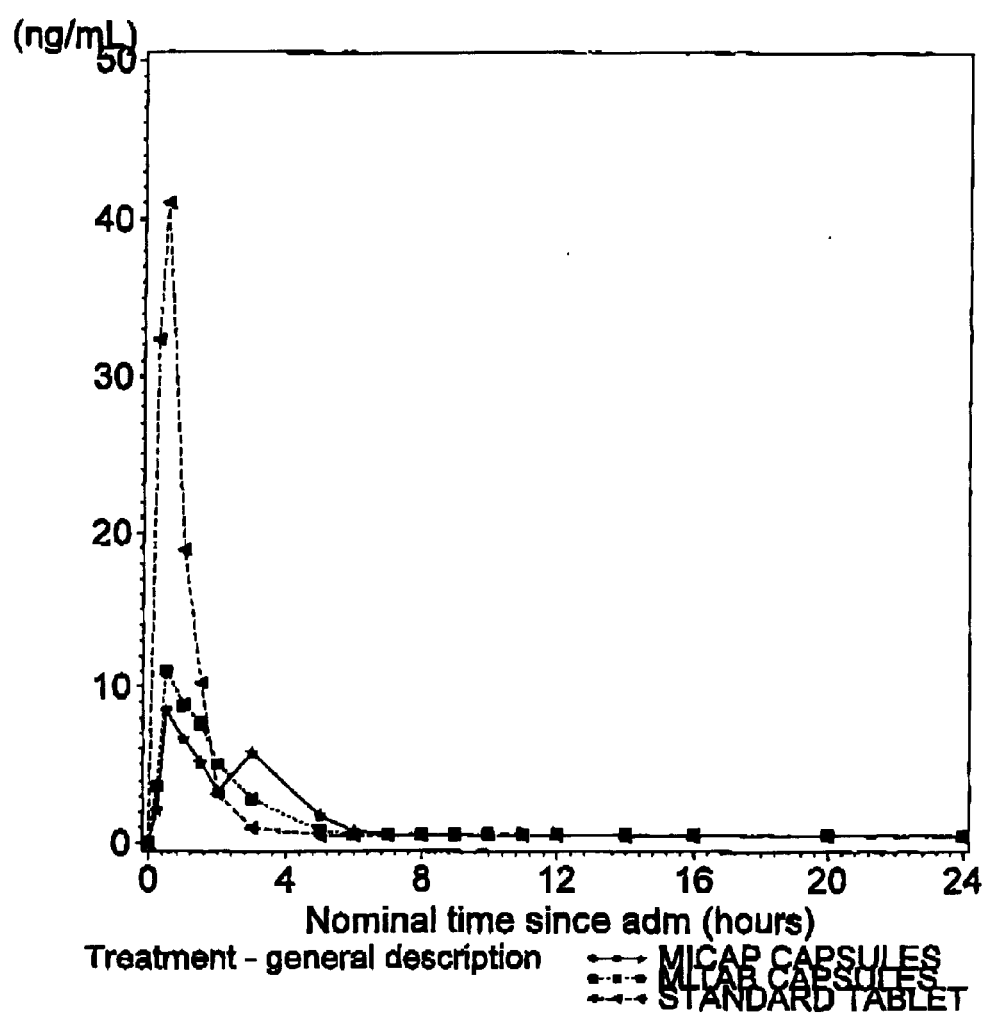
FIG. 23 illustrates the results of Example 14.

The results are also shown in FIG. 22.

Example 15

Pilot Bioavailability Study of Two Prototypes of Midodrine Controlled Release Formulations Compared to Standard Formulation (Tablet) in Healthy Volunteers Introduction Systolic blood pressure is transiently and minimally decreased in normal individuals when rising to upright position. Normal physiologic feedback mechanisms work through neurally mediated pathways to maintain the standing blood pressure and thus support adequate cerebral perfusion. These compensatory mechanisms that regulate blood pressure when standing are deficient in patients with orthostatic hypotension, a condition that may lead to inadequate cerebral perfusion with accompanying symptoms of syncope, dizziness/light-headedness and blurred vision, among others.

Midodrine is a prodrug labeled for treatment of orthostatic hypotension. After absorption it is readily metabolized to desglymidodrine that acts as an agonist at the peripheral α-1 receptors in the smooth muscles of arteries and veins, but has no direct central nervous or cardiac effects. Its main effect is to increase the vascular tone thus increasing the total peripheral resistance and rising blood pressure. The pressor effect of midodrine is manifest within 20 to 90 minutes after oral administration of a single dose. This pressor effect usually persists for 3 to 6 hours. Doses used in clinical practise (10 mg t.i.d.) significantly increase standing blood pressure, thus alleviating symptoms of orthostatic hypotension.

Controlled Release Formulation

The rationale of the development of a controlled release formulation is to reduce the number of dosings during the day and to avoid major changes in plasma concentration of desglymidodrine. This will increase compliance and reduces changes in severity of symptoms of orthostatic hypotension and thus possibly increase quality of life.

Two prototypes have been developed according to the present invention. One prototype "Micap" is a multiple unit formulation (see Example 12), each unit releasing its amount of midodrine dependent on the acidity of the environment. As the acidity is different in different parts of the gut the result is a continuous release during the passage. The other prototype "Mitab" is composed of three layers releasing midodrine differently creating a time-dependent release (see Example 2). The strength of the controlled release formulations has been chosen to 5 mg to allow for individual titration of the total daily dose. The study is a pilot trial of the bioavailability of the two prototypes compared to a standard tablet.

Objective

To determine the bioavailability of two novel prototypes of controlled release formulations of midodrine hydrochloride compared to standard tablets.

Trial Design

Open-labeled randomized 3 way cross-over trial. All subjects were administered 10 mg midodrine hydrochloride either as a standard tablet or as one of two novel controlled release formulations at three occasions distributed 3 days apart.

Trial Population

Eight healthy volunteers, both genders, 18–55 years of age, normal weight, informed consent, not pregnant or lactating, not trying to become pregnant, no liver, renal or gastrointestinal disease that may influence pharmacokinetics or the health of the volunteers, no history of alcohol and drug abuse, non-smokers.

Assessments $AUC_t$ (area under the plasma concentration curve to time t), $C_{max}$ (peak (or shoulder or plateau) plasma concentration), $t_{max}$ (time to peak (or shoulder or plateau) plasma concentration), MRT (mean residence time), $t_{>75\% \ Cmax}$ ($W_{75}$—duration of plasma concentration above 75% of $C_{max}$), HVD ($W_{50}$—half value duration) and time to a possible second peak (or shoulder or plateau) were calculated for midodrine and its biologically active metabolite, desglymidodrine. $AUC_{infinity}$ (area under the plasma concentration curve extrapolated to infinity) and $t_{1/2}$ (plasma concentration half life) are calculated, whenever relevant.

Whenever, the concentration went under the detection limit, the values were set to ½×detection limit, i.e. for midodrine ½×1 ng/ml and for desglymidodrine ½×0.5 ng/ml. Because of such a contribution to the AUC, $AUC_{24}$ was often larger than $AUC_{infinity}$.

Trial Products

Midodrine tablets 5 mg, Gutron from Nycomed, Denmark, midodrine controlled release formulation (pH dependent release) prepared as described in Example 12, 5 mg, and midodrine controlled release formulation (time dependent release) prepared as described in Example 2, 5 mg.

Food and Liquid

The subjects were fasting from 8 hours before dosing until 3 hours post dosing. Water was allowed until 1 hour before dosing. No alcoholic beverages or beverages containing caffeine (coffee, tea or cola) are allowed from 8 hours before dosing until last blood sample has been drawn (24 hours).

Study drug was administered to the subjects with 150 ml of water. Additional 150 ml of water was administered to the subjects 1 and 2 hours after dosing.

Meals were standardized throughout all 3 study visits and served according to the following schedule:

4 hours after dosing: lunch
7 hours after dosing: snack
10 hours after dosing: dinner
14 hours after dosing: snack Study Drug Two tablets or capsules of study drug (midodrine tablets, Mitab or Micap) (total dose 10 mg) were administered between 7.30 and 8.30 am. Administration of study drug is followed by at least three days washout.

Blood Samples

Seven ml of venous blood were withdrawn immediately before dosing, and at 15 and 30 minutes, 1, 1.5, 2, 3, 5, 6, 7, 8, 9, 10, 11, 12, 14, 16, 20 and 24 hours after dosing. The blood samples were placed on ice immediately after drawing and centrifuged and frozen within 20 minutes. Analysis for midodrine and desglymidodrine was performed by HPLC with fluorescence detection. The analyses were performed by Quintiles AB, Uppsala, Sweden.

Results

Figure 24:
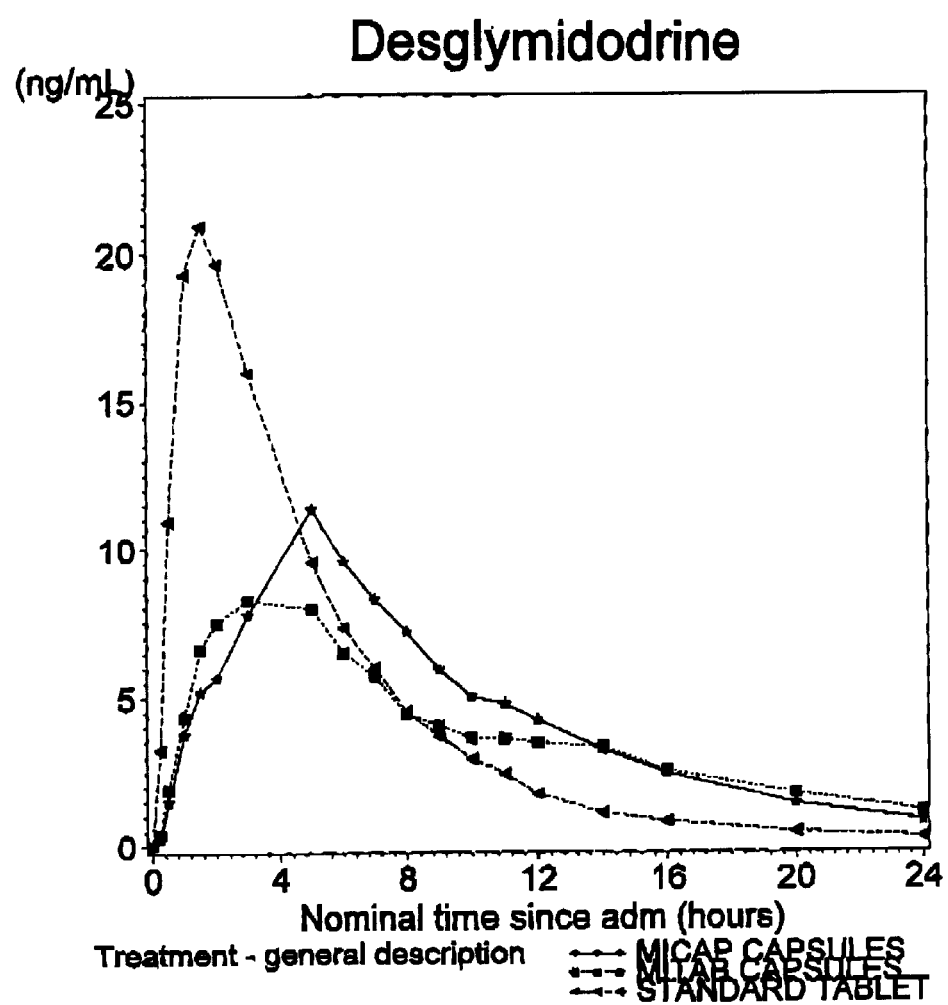
Figure 25:
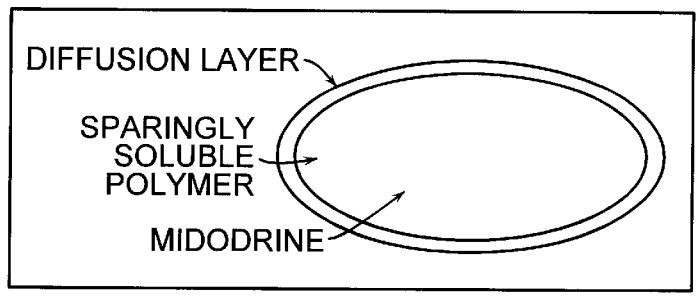
FIG. 25 illustrates a formulation comprising a coated matrix and a sparingly soluble and/or swellable polymer comprising midodrine or another appropriate ingredient such as desglymidodrine.
Figure 26:
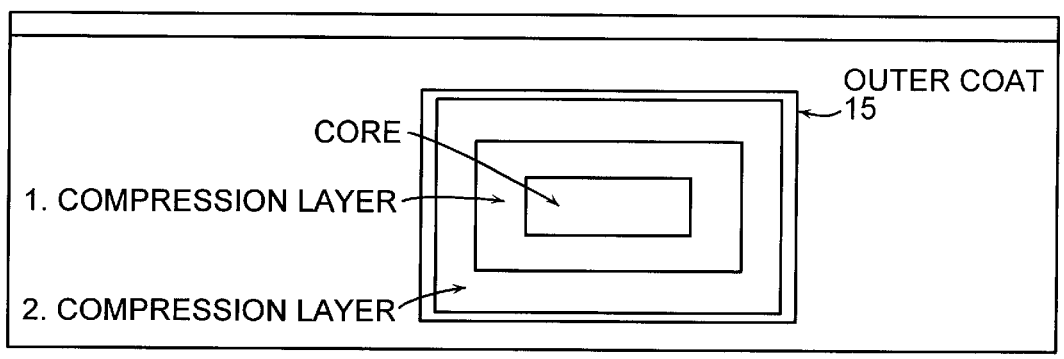
FIG. 26 illustrates a formulation comprising a polymer core comprising midodrine which is compression coated with one or more coatings which also comprise midodrine.

The mean plasma concentration curves for midodrine and desglymidodrine, respectively, are shown in FIGS. 24 and 25. The measured and calculated parameters for each composition (n=7 for Micap and Mitab, n=8 for standard tablets) are given in the following.

AUC and MRT have been calculated using the trapezoidal rule and the AUMC method (Yamaoka K., Nakagawa T., Uno T.: Statistical moments in pharmacokineics, J. Pharmacokin. Biopharm. 1978: 6:647–58).

For extrapolation to infinity (the tail) the following formulas have been used:

$$C_p/k_e \text{ (for AUC) and } nC_p/(k_e^2) \text{ (for AUMC)}$$

Where
$C_p$=the last measured plasma concentration
$k_e$=the elimination rate constant
N=the time for last data point with measurable concentrations.

Midodrine ng/ml, mean values (standard deviation):

|  | Micap | Mitab | Standard tablets |
| --- | --- | --- | --- |
| $AUC_{24}$ | 32.8 (6.7) | 32.7 (12.1) | 51.7 (13.5) |
| $C_{max}$ | 10.0 (2.6) | 12.8 (6.5) | 41.4 (12.6) |
| $t_{max}$ | 0.7 (0.4) | 0.9 (0.5) | 0.5 (0.2) |
| MRT | 3.0 (0.4) | 2.3 (0.3) | 1.0 (0.2) |
| HVD | 2.6 (1.1) | 1.5 (0.8) | 0.9 (0.3) |
| $t_{>75\% Cmax}$ | 1.0 (1.0) | 0.8 (0.6) | 0.5 (0.1) |
| $AUC_{infinity}$ | 24.1 (6.7) | 21.8 (13.1) | 41.3 (14.0) |

Desglymidodrine ng/ml, mean values (standard deviation):

|  | Micap | Mitab | Standard tablets |
| --- | --- | --- | --- |
| $AUC_{24}$ | 106.0 (29.1) | 92.7 (36.4) | 114.4 (31.9) |
| $C_{max}$ | 11.4 (3.2) | 8.7 (5.0) | 21.7 (5.1) |
| $t_{max}$ | 5.0 (0.0) | 2.9 (1.1) | 1.4 (0.4) |
| MRT | 9.5 (1.0) | 11.8 (4.1) | 4.7 (0.5) |
| HVD | 7.7 (0.4) | 9.9 (4.1) | 4.1 (0.4) |
| $t_{>75\% Cmax}$ | 3.4 (0.3) | 4.4 (0.5) | 2.1 (0.4) |
| $AUC_{infinity}$ | 111.5 (33.9) | 104.1 (36.9) | 112.9 (32.5) |

Sum of midodrine and desglymidodrine nmol/l, mean values (standard deviation):

|  | Micap | Mitab | Standard tablets |
| --- | --- | --- | --- |
| $AUC_{24}$ | 566.1 (145.6) | 509.1 (195.2) | 667.3 (176.4) |
| $C_{max}$ | 60.5 (14.5) | 66.0 (29.7) | 195.1 (51.9) |
| $t_{max}$ | 3.0 (1.7) | 1.3 (0.9) | 0.6 (0.2) |
| MRT | 9.7 (1.0) | 12.4 (4.5) | 4.6 (0.6) |
| HVD | 7.7 (0.8) | 5.0 (2.5) | 1.9 (0.8) |
| $t_{>75\% Cmax}$ | 4.4 (1.2) | 1.8 (1.3) | 0.9 (0.4) |
| $AUC_{infinity}$ | 608.7 (172.8) | 588.2 (190.1) | 661.1 (183.3) |

Midodrine nmol/l, mean values (standard deviation)

|  | Micap | Mitab | Standard tablets |
| --- | --- | --- | --- |
| $AUC_{24}$ | 112.7 (23.2) | 112.5 (41.6) | 178.0 (46.4) |
| $C_{max}$ | 34.3 (9.1) | 43.9 (22.4) | 142.3 (49.5) |
| $t_{max}$ | 0.7 (0.4) | 0.9 (0.5) | 0.5 (0.2) |
| MRT | 3.0 (0.4) | 2.3 (0.3) | 1.0 (0.2) |
| HVD | 2.6 (1.1) | 1.5 (0.8) | 0.9 (0.3) |
| $t_{>75\% Cmax}$ | 1.0 (1.0) | 0.8 (0.6) | 0.5 (0.1) |
| $AUC_{infinity}$ | 83.0 (23.1) | 74.9 (45.0) | 142.1 (48.2) |

Desglymidodrine nmol/l, mean values (standard deviation):

|  | Micap | Mitab | Standard tablets |
| --- | --- | --- | --- |
| $AUC_{24}$ | 453.4 (124.7) | 396.6 (156.0) | 489.4 (136.5) |
| $C_{max}$ | 48.6 (13.5) | 37.4 (21.5) | 92.9 (22.0) |
| $t_{max}$ | 5.0 (0.0) | 2.9 (1.1) | 1.4 (0.4) |
| MRT | 9.5 (1.0) | 11.8 (4.1) | 4.7 (0.5) |
| HVD | 7.7 (0.4) | 9.9 (4.1) | 4.1 (0.4) |
| $t_{>75\% Cmax}$ | 3.4 (0.3) | 4.4 (0.5) | 2.1 (0.4) |
| $AUC_{infinity}$ | 477.2 (144.9) | 445.4 (157.7) | 483.3 (138.9) |

Furthermore, the time interval in which the concentration of midodrine, desglymidodrine or the sum of midodrine and desglymidodrine is at a constant value±40% has been determined. The time interval is found by looking at all possible time intervals (using the time points from the blood sampling) of all possible lengths. For each time interval the mean is calculated and it is checked whether all plasma concentration points in that time interval is lying within ±40% of the mean value. The time interval in question is the longest time interval for which all concentration points in the interval lie within the mean of the time interval ±40%. In order to get a relevant interval the constant value minus 40% has to be higher than the detection limit. The interval is calculated for each patient and the mean value of the length of time interval is given.

For example, for patient 1 the MICAP capsules gave a mean plasma concentration of desglymidodrine at 8.5 ng/ml in the time interval from 2 hours to 9 hours (i.e. a 7 hours interval). In this period the maximum plasma concentration of desglymidodrine was measured as 11.8 ng/ml and the minimum plasma concentration as 5.5 ng/ml Since 8.5 ng/ml+40% is 11.9 ng/ml and 8.5 ng/ml−40% is 5.1 ng/ml all measured plasma concentration points in that particular interval lie within the mean value±40%. Since this was the longest time interval where all concentration points lie within the mean±40% the resulting time interval for the MICAP capsules for patient 1 was 7 hours.

The following results were obtained:

Time interval (hours) where the concentration of midodrine lies at a constant value±40%:

| Micap (n = 7) | 1.7 |
| --- | --- |
| Mitab (n = 7) | 1.4 |
| Standard tablets (n = 8) | 0.63 |

Time interval (hours) where the concentration of desglymidodrine lies at a constant value±40%:

| | |
|---|---|
| Micap (n = 7) | 6.3 |
| Mitab (n = 7) | 11.5 |
| Standard tablets (n = 8) | 3.7 |

Time interval (hours) where the sum of the concentration of midodrine and desglymidodrine lies at a constant value±40%:

| | |
|---|---|
| Micap (n = 7) | 7.5 |
| Mitab (n = 7) | 11.9 |
| Standard tablets (n = 8) | 3.5 |

The aim of the pilot study was to test the bioavailability of the two novel compositions and a standard Gutron tablet and to estimate whether the compositions are bioequivalent.

Furthermore, the controlled release properties of the novel compositions as compared to the standard composition (Gutron tablet) can be depicted from the data generated.

The values of $C_{max}$ and $AUC_{0-24}/AUC_{infinity}$ of the standard tablet are greater than the same values of each of the two prototypes considering the plasma values of midodrine, desglymidodrine and the sum of the two. It is expected that $C_{max}$ is lower in controlled release compositions than in plain release compositions as this reflects a lesser degree of fluctuation of plasma values. This is one of the purposes of a controlled release composition. It is further supported by the prolongation of the time interval in which the plasma values of midodrine, desglymidodrine and the sum of the concentrations of the two lie at a constant value.

The sum of the plasma concentrations of midodrine and the active metabolite desglymidodrine reflects the total amount of drug absorbed into the blood stream. The values of $T_{max}$ $W_{50}$ and $T_{>75\% \ cmax}$ ($W_{75\%}$) and MRT for this sum concentration are more than 2 times greater of the novel controlled release compositions than the values of the standard tablet. The prolongation of the above mentioned values means that the active drug substance resides in the plasma for a longer time period reducing the numbers of daily dosing needed. Thus, another purpose of a controlled release composition is fulfilled.

Conclusion

Based on the AUC values, the bioavailabilities of the novel controlled release compositions are lesser than the bioavailability of the standard tablet indicating that the content of active drug substance in the controlled release compositions should be increased to establish bioequivalence.

The novel compositions possess controlled release properties as compared to the standard tablet for reasons discussed above.

What is claimed is:

1. A controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof,
    wherein the in vitro release rate of midodrine and/or desglymidodrine has the following course of events
    i) a relatively fast first initial release followed by
    ii) a steady release or a slower release than in step i) above, which is followed by
    iii) a second rise in release rate that takes place 5–10 hours after start of an in vitro dissolution test and, finally,
    iv) a decline in release rate
wherein the composition upon administration provides a relatively fast peak plasma concentration of desglymidodrine, and a therapeutically effective plasma concentration of desglymidodrine is maintained for at least about 9 hours.

2. A controlled release pharmaceutical composition according to claim 1, wherein
    the relatively fast peak plasma concentration of desglymidodrine is obtained about 15 minutes–6 hours after oral administration.

3. A composition according to claim 1, wherein the plasma concentration of desglymidodrine is maintained at a therapeutically active level for about 4.5–14 hours.

4. A composition according to claim 1, wherein the plasma concentration of desglymidodrine is maintained at a relatively constant level for about 4.5–16 hours.

5. A composition according to claim 4, wherein the relatively constant level n is ±60%, and wherein n is the plasma concentration in ng/ml and monitored in healthy persons.

6. A composition according to claim 1 containing midodrine or a pharmaceutically acceptable salt thereof.

7. A composition according to claim 6, wherein the plasma concentration of midodrine after oral administration is maintained at a relatively constant level for about 0.7–4 hours.

8. A composition according to claim 7, wherein the relatively constant level m is ±60%, and wherein m is the plasma concentration in ng/ml and monitored in healthy persons.

9. A composition according to claim 6, wherein the release pattern of midodrine from the composition—when tested in vitro using Dissolution Method I or II and employing a basket according to USP and Ph. Eur, 100 rpm, 600 ml 1 N hydrochloric acid as dissolution medium and a temperature of 37° C.—is:
    1–15% w/w is released from the composition within the first 30 min after start of the test,
    10–35% w/w is released about 30 min after start of the test,
    15–40% w/w is released about 1 hour after start of the test,
    20–50% w/w is released about 2 hours after start of the test,
    20–55% w/w is released about 3 hours after start of the test,
    25–75% w/w is released about 4 hours after start of the test,
    30–74% w/w is released about 6 hours after start of the test,
    40–85% w/w is released about 8 hours after start of the test,
    65–100% w/w is released about 10 hours after start of the test, and
    90–110% w/w is released about 12 hours after start of the test.

10. A composition according to claim 6, wherein the release pattern of midodrine from the composition—when tested in vitro using Dissolution Method III or IV described herein and employing a basket according to USP and Ph. Eur, 100 rpm, a first dissolution medium with a pH of about 1.0 for the first 2 hours of the testing followed by a second dissolution medium with a pH of about 6.0 for the next 5.5 hours and finally a third dissolution medium with a pH of about 7.5 until the end of the testing, and a temperature of 37° C.—is:

1–15% w/w is released from the composition within the first 30 min after start of the test,
10–35% w/w is released about 30 min after start of the test,
15–40% w/w is released about 1 hour after start of the test
20–50% w/w is released about 2 hours after start of the test,
20–55% w/w is released about 3 hours after start of the test,
25–75% w/w is released about 4 hours after start of the test,
30–74% w/w is released about 6 hours after start of the test,
40–95% w/w is released about 8 hours after start of the test,
65–100% w/w is released about 10 hours after start of the test, and
75–110% w/w is released about 12 hours after start of the test.

11. A composition according to claim 6, wherein the release pattern of midodrine from the composition—when tested in vitro employing an in vitro dissolution method is:

1–15% w/w is released from the composition within the first 30 min after start of the test,
10–35% w/w is released about 30 min after start of the test,
15–40% w/w is released about 1 hour after start of the test,
20–50% w/w is released about 2 hours after start of the test,
20–55% w/w is released about 3 hours after start of the test,
25–75% w/w is released about 4 hours after start of the test,
30–74% w/w is released about 6 hours after start of the test,
35–85% w/w is released about 7 hours after start of the test,
45–95% w/w is released about 8 hours after start of the test,
65–100% w/w is released about 10 hours after start of the test, and
90–110% w/w is released about 12 hours after start of the test.

12. A composition according to claim 6, wherein the release pattern of midodrine from the composition—when tested in vitro employing an in vitro dissolution method is as follows (±30% w/w of the values stated below):

about 25% w/w is released about 30 min after start of the test,
about 35% w/w is released about 1 hour after start of the test,
about 39% w/w is released about 2 hours after start of the test,
about 47% w/w is released about 3 hours after start of the test,
about 53% w/w is released about 4 hours after start of the test,
about 66 w/w is released about 6 hours after start of the test,
about 75% w/w is released about 7 hours after start of the test,
about 80% w/w is released about 8 hours after start of the test, and
about 90% w/w is released about 10 hours after start of the test, and
about 100% w/w is released about 12 hours after start of the test.

13. A composition according to claim 1, wherein the steady release period ii) starts about 1–3 hours after start of the test.

14. A composition according to claim 1 or 13, wherein the steady release period ii) is maintained for at least 2 hours.

15. The composition according to claim 1, wherein the second rise in release rate takes place 5–10 hours after start of the in vitro release.

16. A composition according to claim 1, wherein the release pattern of midodrine and/or desglymidodrine from the composition—when tested in vitro employing any Dissolution Method as described herein,—is as follows (±30% w/w of the values stated below):

about 25% w/w is released about 30 min after start of the test,
about 35% w/w is released about 1 hour after start of the test,
about 39% w/w is released about 2 hours after start of the test,
about 47% w/w is released about 3 hours after start of the test,
about 53–56% w/w is released about 4 hours after start of the test,
about 66–72% w/w is released about 6 hours after start of the test,
about 80–85% w/w is released about 8 hours after start of the test,
about 93% w/w is released about 10 hours after start of the test, and
about 100% w/w is released about 12 hours after start of the test.

17. A composition according to claim 1, wherein the release pattern of midodrine and/or desglymidodrine from the composition—when tested in vitro employing any Dissolution Method as described herein—is as follows (±30% w/w of the values stated below):

about 28% w/w is released about 30 minutes after start of the test,
about 35% w/w is released about 1 hour after start of the test,
about 41% w/w is released about 2 hours after start of the test,
about 45% w/w is released about 3 hours after start of the test,
about 55% w/w is released about 4 hours after start of the test,
about 70 w/w is released about 6 hours after start of the test,
about 78% w/w is released about 7 hours after start of the test, and
about 90% w/w is released about 8 hours after start of the test,
about 95% w/w is released about 10 hours after start of the test, and
about 100% w/w is released about 12 hours after start of the test.

18. A controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof,
wherein the in vitro release rate of midodrine and/or desglymidodrine has the following course of events
i) a relatively fast first initial release followed by
ii) a steady release or a slower release than in step i) above, which is followed by
iii) a second rise in release rate that takes place 5–10 hours after start of an in vitro test and, finally,
iv) a decline in release rate
and wherein the release pattern of midodrine and/or desglymidodrine from the composition—when tested in vitro employing an in vitro dissolution Method as described herein,—is as follows (±30% w/w of the values stated below):
about 25% w/w is released about 30 min after start of the test,
about 35% w/w is released about 1 hour after start of the test,
about 39% w/w is released about 2 hours after start of the test,
about 47% w/w is released about 3 hours after start of the test,
about 53–56% w/w is released about 4 hours after start of the test,
about 66–72% w/w is released about 6 hours after start of the test,
about 80–85% w/w is released about 8 hours after start of the test,
about 93% w/w is released about 10 hours after start of the test, and
about 100% w/w is released about 12 hours after start of the test.

19. A controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof,
wherein the in vitro release rate of midodrine and/or desglymidodrine has the following course of events
i) a relatively fast first initial release followed by
ii) a steady release or a slower release than in step i) above, which is followed by
iii) a second rise in release rate that takes place 5–10 hours after start of an in vitro test and, finally,
iv) a decline in release rate
and wherein the release pattern of midodrine and/or desglymidodrine from the composition—when tested in vitro employing an in vitro dissolution method as described herein—is as follows (±30% w/w of the values stated below):
about 28% w/w is released about 30 min after start of the test,
about 35% w/w is released about 1 hour after start of the test,
about 41% w/w is released about 2 hours after start of the test,
about 45% w/w is released about 3 hours after start of the test,
about 55% w/w is released about 4 hours after start of the test,
about 70 w/w is released about 6 hours after start of the test,
about 78% w/w is released about 7 hours after start of the test,
about 90% w/w is released about 8 hours after start of the test,
about 95% w/w is released about 10 hours after start of the test, and
about 100% w/w is released about 12 hours after start of the test.

20. A composition according to claim 18 or 19, wherein the composition upon administration results in a relatively fast peak plasma concentration of desglymidodrine, and a therapeutically effective plasma concentration of desglymidodrine is maintained for at least about 9 hours.

21. A composition according to claim 20, wherein the steady release period ii) starts about 1–3 hours after start of the test.

22. A composition according to claim 20, wherein the steady release period ii) is maintained for at least 2 hours.

23. A method for treating a patient suffering from syncope, the method comprising administering an effective amount of midodrine and/or desglymidodrine in the form of a controlled release composition according to claim 1 to a patient in need thereof.

24. A method for treating a patient suffering from orthostatic hypotension and/or urinary incontinence, the method comprising administering an effective amount of midodrine and/or desglymidodrine in the form of a controlled release composition according to claim 1 to a patient in need thereof.

25. A method of claim 24, wherein the patient is suffering from orthostatic hypotension.

26. A method of claim 24, wherein the patient is suffering from urinary incontinence.

27. A method of claim 24, wherein the patient is suffering from urinary stress incontinence.

* * * * *